(12) United States Patent
Rossetti et al.

(10) Patent No.: US 7,705,016 B2
(45) Date of Patent: Apr. 27, 2010

(54) REGULATION OF FOOD INTAKE BY MODULATION OF LONG-CHAIN FATTY ACYL-COA LEVELS IN THE HYPOTHALAMUS

(75) Inventors: Luciano Rossetti, Bedford Hills, NY (US); Silvana Obici, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 10/545,056

(22) PCT Filed: Feb. 12, 2004

(86) PCT No.: PCT/US2004/004344

§ 371 (c)(1),
(2), (4) Date: Apr. 27, 2006

(87) PCT Pub. No.: WO2004/071458

PCT Pub. Date: Aug. 26, 2004

(65) Prior Publication Data

US 2007/0093434 A1    Apr. 26, 2007

Related U.S. Application Data

(60) Provisional application No. 60/447,138, filed on Feb. 13, 2003.

(51) Int. Cl.
A61K 31/44 (2006.01)
A61K 31/41 (2006.01)
A61K 31/27 (2006.01)
A61K 31/17 (2006.01)
A61K 31/20 (2006.01)

(52) U.S. Cl. .................. 514/305; 514/357; 514/381; 514/476; 514/588; 514/560

(58) Field of Classification Search .......... 514/305, 514/357, 381, 476, 588, 560, 909, 866
See application file for complete search history.

(56) References Cited

U.S. PATENT DOCUMENTS

| | | | |
|---|---|---|---|
| 4,196,300 A | 4/1980 | Mohrbacher et al. |
| 4,324,796 A | 4/1982 | Eistetter et al. |
| 4,334,089 A | 6/1982 | Kraas et al. |
| 4,337,267 A | 6/1982 | Eistetter et al. |
| 4,370,343 A | 1/1983 | Mohrbacher et al. |
| 4,430,339 A | 2/1984 | Eistetter et al. |
| 4,472,432 A | 9/1984 | Iwamura et al. |
| 4,558,050 A | 12/1985 | Stacpoole |
| 4,631,294 A | 12/1986 | Barsan |
| 4,724,230 A | 2/1988 | Cone, Jr. |
| 4,788,304 A | 11/1988 | Marshall et al. |
| 4,788,306 A | 11/1988 | Schiehser et al. |
| 4,933,365 A | 6/1990 | Marshall et al. |
| 4,935,450 A | 6/1990 | Cone, Jr. |
| 4,946,866 A | 8/1990 | Wolf et al. |
| 5,145,611 A | 9/1992 | Wolff et al. |
| 5,145,871 A | 9/1992 | Cavazza |
| 5,179,079 A | 1/1993 | Hansen et al. |
| 5,196,418 A | 3/1993 | Gandour et al. |
| 5,231,988 A | 8/1993 | Wernicke et al. |
| 5,263,480 A | 11/1993 | Wernicke et al. |
| 5,284,845 A | 2/1994 | Paulsen |
| 5,422,115 A | 6/1995 | Horrobin |
| 5,561,165 A | 10/1996 | Lautt et al. |
| 5,587,397 A | 12/1996 | Fox |
| 5,589,183 A | 12/1996 | Jannetta |
| 5,643,951 A | 7/1997 | Stacpoole et al. |
| 5,739,159 A | 4/1998 | Wolf |
| 5,759,837 A | 6/1998 | Kuhajda et al. |
| 5,798,348 A | 8/1998 | Alemany |
| 5,804,212 A | 9/1998 | Illum |
| 5,844,102 A | 12/1998 | Sierks et al. |
| 5,855,917 A | 1/1999 | Cook et al. |
| 5,886,037 A | 3/1999 | Klor et al. |
| 5,889,002 A | 3/1999 | Nielsen et al. |
| 5,902,789 A | 5/1999 | Stoltz |
| 5,916,910 A | 6/1999 | Lai |
| 5,981,575 A | 11/1999 | Kuhajda et al. |
| 5,990,092 A | 11/1999 | Walsh |
| 5,998,463 A | 12/1999 | Hulin et al. |
| 6,013,666 A | 1/2000 | Jew et al. |

(Continued)

FOREIGN PATENT DOCUMENTS

WO    WO 98/35952    8/1998

(Continued)

OTHER PUBLICATIONS

International Search Report and the Written Opinion of the International Searching Authority for PCT Application No. PCT/US04/04344 dated Dec. 15, 2005.

(Continued)

*Primary Examiner*—Kevin Weddington
(74) *Attorney, Agent, or Firm*—Amster, Rothstein & Ebenstein LLP

(57) ABSTRACT

Methods of reducing food intake and glucose production in a mammal, or restoring hepatic autoregulation are provided. The methods involve increasing long-chain fatty acyl-Co-A (LC-CoA) levels in the hypothalamus, or stimulating efferent fibers in the hepatic branch of the vagus nerve. Also provided are methods of increasing food intake and glucose production in a mammal. The methods involve decreasing long-chain fatty acyl-Co-A (LC-CoA) levels in the hypothalamus of the mammal.

3 Claims, 9 Drawing Sheets

U.S. PATENT DOCUMENTS

| | | | |
|---|---|---|---|
| 6,030,613 A | 2/2000 | Blumberg et al. | |
| 6,030,993 A | 2/2000 | Jew et al. | |
| 6,054,480 A | 4/2000 | Cairns et al. | |
| 6,107,329 A | 8/2000 | Hoover et al. | |
| 6,150,526 A | 11/2000 | Binggeli et al. | |
| 6,197,765 B1 | 3/2001 | Vardi et al. | |
| 6,232,310 B1 | 5/2001 | Hansen et al. | |
| 6,297,269 B1 | 10/2001 | Hulin et al. | |
| 6,313,112 B1 | 11/2001 | Busija | |
| 6,331,559 B1 | 12/2001 | Bingham et al. | |
| 6,356,788 B2 | 3/2002 | Boveja | |
| 6,365,628 B1 | 4/2002 | Berge | |
| 6,369,073 B1 * | 4/2002 | Giannessi et al. | 514/305 |
| 6,369,075 B1 | 4/2002 | Ruggeri et al. | |
| 6,399,601 B1 | 6/2002 | Du Bois | |
| 6,407,135 B1 | 6/2002 | Lai et al. | |
| 6,410,046 B1 | 6/2002 | Lerner | |
| 6,417,232 B1 | 7/2002 | Berge | |
| 6,420,354 B1 | 7/2002 | Marquess et al. | |
| 6,423,705 B1 | 7/2002 | Tracey et al. | |
| 6,440,966 B1 | 8/2002 | Barrett et al. | |
| 6,441,015 B2 | 8/2002 | Aspnes et al. | |
| 6,441,036 B1 | 8/2002 | Berge | |
| 6,444,701 B1 * | 9/2002 | Giannessi et al. | 514/476 |
| 6,451,783 B1 | 9/2002 | Hadcock et al. | |
| 6,479,676 B1 | 11/2002 | Wolf | |
| 6,485,726 B1 | 11/2002 | Blumberg et al. | |
| 6,521,617 B2 | 2/2003 | Marban et al. | |
| 6,555,579 B2 | 4/2003 | Kritchevsky | |
| 6,564,101 B1 | 5/2003 | Zikria | |
| 6,572,542 B1 | 6/2003 | Houben et al. | |
| 6,576,653 B2 | 6/2003 | Du Bois | |
| 6,587,719 B1 | 7/2003 | Barrett et al. | |
| 6,609,025 B2 | 8/2003 | Barrett et al. | |
| 6,610,746 B2 | 8/2003 | Fryburg et al. | |
| 6,615,081 B1 | 9/2003 | Boveja | |
| 6,620,830 B2 | 9/2003 | Chiang | |
| 6,630,157 B1 | 10/2003 | Horrobin et al. | |
| 6,649,634 B2 | 11/2003 | Hoover et al. | |
| 6,653,314 B2 | 11/2003 | Cheng et al. | |
| 6,664,291 B2 | 12/2003 | Chiang et al. | |
| 6,670,481 B2 | 12/2003 | Wolf | |
| 6,684,105 B2 | 1/2004 | Cohen et al. | |
| 6,699,832 B2 | 3/2004 | Hadcock | |
| 6,699,904 B2 | 3/2004 | Hayward et al. | |
| 6,706,892 B1 | 3/2004 | Ezrin et al. | |
| 6,712,802 B1 | 3/2004 | Cairns et al. | |
| 6,720,351 B2 | 4/2004 | Bertinato et al. | |
| 6,723,744 B2 | 4/2004 | Aspnes et al. | |
| 6,734,175 B2 | 5/2004 | Hadcock et al. | |
| 6,770,466 B2 | 8/2004 | Shi et al. | |
| 6,778,854 B2 | 8/2004 | Puskas | |
| 6,787,652 B1 | 9/2004 | Dow et al. | |
| 6,803,457 B2 | 10/2004 | DeNinno et al. | |
| 6,815,451 B2 | 11/2004 | Velker et al. | |
| 6,821,977 B2 | 11/2004 | Gammill | |
| 6,826,428 B1 | 11/2004 | Chen et al. | |
| 6,828,343 B2 | 12/2004 | Du Bois | |
| 6,832,114 B1 | 12/2004 | Whitehurst et al. | |
| 6,852,760 B1 | 2/2005 | Fine et al. | |
| 6,864,268 B2 | 3/2005 | Lafontaine et al. | |
| 6,867,184 B2 | 3/2005 | Treadway | |
| 6,867,210 B2 | 3/2005 | Hogenkamp et al. | |
| 6,913,763 B2 | 7/2005 | Lerner | |
| 2002/0013268 A1 | 1/2002 | Fryburg et al. | |
| 2002/0016344 A1 | 2/2002 | Tracey | |
| 2002/0052348 A1 | 5/2002 | Giannessi et al. | |
| 2002/0087192 A1 | 7/2002 | Barrett et al. | |
| 2002/0091144 A1 | 7/2002 | Marban et al. | |
| 2002/0099075 A1 | 7/2002 | Tracey et al. | |
| 2002/0112253 A1 | 8/2002 | Wakil et al. | |
| 2002/0116030 A1 | 8/2002 | Rezai | |
| 2002/0183369 A1 | 12/2002 | Du Bois | |
| 2002/0183683 A1 | 12/2002 | Lerner | |
| 2002/0187534 A1 | 12/2002 | Pizer et al. | |
| 2002/0198382 A1 | 12/2002 | Wolf | |
| 2003/0018367 A1 | 1/2003 | DiLorenzo | |
| 2003/0036199 A1 | 2/2003 | Bamdad et al. | |
| 2003/0040774 A1 | 2/2003 | Terry et al. | |
| 2003/0055021 A1 | 3/2003 | DeNinno et al. | |
| 2003/0073127 A1 | 4/2003 | Ji et al. | |
| 2003/0078623 A1 | 4/2003 | Weinberg et al. | |
| 2003/0087896 A1 | 5/2003 | Glover | |
| 2003/0144350 A1 | 7/2003 | Stevenson et al. | |
| 2003/0144709 A1 | 7/2003 | Zabara et al. | |
| 2003/0181958 A1 | 9/2003 | Dobak | |
| 2003/0181959 A1 | 9/2003 | Dobak | |
| 2003/0187254 A1 | 10/2003 | Perry et al. | |
| 2003/0195361 A1 | 10/2003 | Du Bois | |
| 2003/0199553 A1 | 10/2003 | Gammill | |
| 2003/0212013 A1 | 11/2003 | Winder | |
| 2003/0212014 A1 | 11/2003 | Ruderman et al. | |
| 2003/0212440 A1 | 11/2003 | Boveja | |
| 2003/0216294 A1 | 11/2003 | Fryburg et al. | |
| 2003/0216792 A1 | 11/2003 | Levin et al. | |
| 2003/0224501 A1 | 12/2003 | Young et al. | |
| 2004/0024065 A1 | 2/2004 | Watkins et al. | |
| 2004/0024428 A1 | 2/2004 | Barrett et al. | |
| 2004/0029784 A1 | 2/2004 | Hathaway | |
| 2004/0038857 A1 | 2/2004 | Tracey | |
| 2004/0039427 A1 | 2/2004 | Barrett | |
| 2004/0054177 A1 | 3/2004 | Otake et al. | |
| 2004/0059383 A1 | 3/2004 | Puskas | |
| 2004/0082576 A1 | 4/2004 | Arrhenius et al. | |
| 2004/0087627 A1 | 5/2004 | Arrhenius et al. | |
| 2004/0092503 A1 | 5/2004 | Arrhenius et al. | |
| 2004/0111139 A1 | 6/2004 | McCreery | |
| 2004/0122074 A1 | 6/2004 | Dow et al. | |
| 2004/0157844 A1 | 8/2004 | Dow et al. | |
| 2004/0157918 A1 | 8/2004 | Loftus et al. | |
| 2004/0172085 A1 | 9/2004 | Knudson et al. | |
| 2004/0176812 A1 | 9/2004 | Knudson et al. | |
| 2004/0198693 A1 | 10/2004 | DeNinno et al. | |
| 2004/0204472 A1 | 10/2004 | Briggs et al. | |
| 2004/0230255 A1 | 11/2004 | Dobak, III | |
| 2004/0235926 A1 | 11/2004 | Sakya | |
| 2004/0249416 A1 | 12/2004 | Yun et al. | |
| 2005/0004173 A1 | 1/2005 | Henkel et al. | |
| 2005/0004621 A1 | 1/2005 | Boveja et al. | |
| 2005/0015129 A1 | 1/2005 | Mische | |
| 2005/0020682 A1 | 1/2005 | Newell et al. | |
| 2005/0026945 A1 | 2/2005 | Kafka et al. | |
| 2005/0026969 A1 | 2/2005 | Cheng et al. | |
| 2005/0032824 A1 | 2/2005 | Cheng et al. | |
| 2005/0032828 A1 | 2/2005 | Cheng et al. | |
| 2005/0038484 A1 | 2/2005 | Knudson et al. | |
| 2005/0049655 A1 | 3/2005 | Boveja et al. | |
| 2005/0176630 A1 | 8/2005 | Cowley et al. | |

FOREIGN PATENT DOCUMENTS

| | | |
|---|---|---|
| WO | WO 99/59957 | 11/1999 |
| WO | WO 02/03978 | 1/2002 |
| WO | WO 02/056022 | 7/2002 |
| WO | WO 03/092694 | 11/2003 |
| WO | WO 2004/003144 | 1/2004 |
| WO | WO 2004/005277 | 1/2004 |
| WO | WO 2004/006835 | 1/2004 |
| WO | WO 2004/031175 | 4/2004 |
| WO | WO 2004/071399 | 8/2004 |
| WO | WO 2004/110368 | 12/2004 |
| WO | WO 2004/110375 | 12/2004 |
| WO | WO 2004/110453 | 12/2004 |
| WO | WO 2004/111199 | 12/2004 |

| | | |
|---|---|---|
| WO | WO 2005/000217 | 1/2005 |
| WO | WO 2005/009950 | 2/2005 |
| WO | WO 2005/009974 | 2/2005 |

OTHER PUBLICATIONS

Al-Ghananeem et al. "Targeted Brain Delivery of 17β-Estradiol Via Nasally Administered Water Soluble Prodrugs" *AAPS PharmSciTech* 3(1): 1-8 (2002).
Barzilai et al. "Leptin Selectively Decreases Visceral Adiposity and Enhances Insulin Action" *Journal of Clinical Investigation* 100(12): 3105-3110 (1997).
Berthoud et al. "Acute Hyperinsulinemia and its Reversal by Vagotomy after Lesions of the Ventromedial Hypothalamus in Anesthetized Rats" *Endocrinology* 105(1): 146-151 (1979).
Brief et al. "Reduction of Food Intake and Body Weight by Chronic Intraventricular Insulin Infusion" *Brain Research Bulletin* 12: 571-575 (1984).
Cinti et al. "Immunohistochemical Localization of Leptin and Uncoupling Protein in White and Brown Adipose Tissue" *Endocrinology* 138(2): 797-804 (1997).
Coleman "Obesity Genes: Beneficial Effects in Heterozygous Mice" *Science* 203(4381): 663-665 (1979).
Frederich et al. "Leptin Levels Reflect Body Lipid Content in Mice: Evidence for Diet-Induced Resistance to Leptin Action" *Nature Medicine* 1(12): 1311-1314 (1995).
Friedman "Obesity in the New Millennium" *Nature* 404: 632-671 (2000).
Hallschmid et al. "Intranasal Insulin Reduces Body Fat in Men But Not in Women" *Diabetes* 53: 3024-3029 (2004).
Inoue et al. "The Effects of Subdiaphragmatic Vagotomy in Rats with Ventromedial Hypothalamic Obesity" *Endocrinology* 100:108-114 (1977).
Kern et al. "Central Nervous System Effects of intranasally Administered Insulin During Euglycemia in Men" *Diabetes* 48: 557-563 (1999).
Liu et al. "Intracerebroventricular Leptin Regulates Hepatic but Not Peripheral Glucose Fluxes" *Journal of Biological Chemistry* 273(47): 31160-31167 (1998).
Makimura et al. "Cerulenin Mimics Effects of leptin on Metabolic Rate, Food Intake, and Body Weight Independent of the Melanocortin System, but Unlike Leptin, Cerulenin Fails to block Neuroendocrine Effects of Fasting" *Diabetes* 50: 733-739 (2001).
Morgan et al. "Central Effects of Oleic Acid on Glucose Production are Nutritionally Regulated" *Keystone Symposium*, Jan. 21-26, 2003, Keystone, Colorado (abstract).
Morgan et al. "Short-term Over-feeding Blunts the Effects of Intracerebroventricular (ICV) Oleic Acid on Hepatic Insulin Action" *Keystone Symposium*, Jan. 10-16, 2002, Keystone, Colorado (abstract).
Neel "The 'Thrifty Genotype' in 1998" *Nutrition Reviews* 57(5): S2-S9 (1999).
Obici et al. "Central Melanocortin Receptors Regulate Insulin Action" *Journal of Clinical Investigation* 108(7): 1079-1085 (2001).
Qi et al. "Long-Chain Polyunsaturated Fatty Acid Accretion in Brain" *Current Opinion in Clinical Nutrition and Metabolic Care* 5:133-138 (2002).
Rapoport "In Vivo Fatty Acid Incorporation into Brain Phosholipids in Relation to Plasma Avallablility, Signal Transduction and Membrane Remodeling" *Journal of Molecular Neuroscience* 16: 243-261 (2001).
Schwartz et al. "Central Nervous System Control of Food Intake" *Nature* 404: 661-671 (2000).
Schwartz et al. "Indentification of Targets of Leptin Action in Rat Hypothalamus" *Journal of Clinical Investigation* 98(5): 1101-1106 (1996).
Schwartz et al. "Specificity of Leptin Action on Elevated Blood Glucose Levels and Hypothalamic Neuropeptide Y Gene Expression in *ob/ob* Mice" *Diabetes* 45: 531-535 (1996).
Shimazu et al. "Hypothalamic Control of Liver Glycogen Metabolism in Adult and Aged Rats" *Brain Research* 144: 343-352 (1978).

Shimomura et al. "Leptin Reverses Insulin Resistance and Diabetes Mellitus in Mice with Congenital Lipodystrophy" *Nature* 401: 73-76 (1999).
Spiegelman et al. "Obesity and the Regulation of Energy Balance" *Cell* 104: 531-543 (2001).
Thupari et al. "C75 Increases Peripheral Energy Utilization and Fatty Acid Oxidation in Diet-Induced Obesity" *PNAS* 99(14): 9498-9502 (2002).
Wang et al. "Interactions Between Leptin and Hypothalamic Neuropeptide Y Neurons in the Control of Food Intake and Energy Homeostasis in the Rat" *Diabetes* 46: 335-341 (1997).
Wang et al. "Overfeeding Rapidly Induces Leptin and Insulin Resistance" *Diabetes* 50: 2786-2791 (2001).
Woods et al. "Chronic Intracerebroventricular Infusion of Insulin Reduces Food Intake and Body Weight of Baboons" *Nature* 282: 503-505(1979).
Woods et al. "Signals that Regulate Food Intake and Energy Homeostasis" *Science* 280: 1378-1383 (1998).
Zhang et al. "Positional Cloning of the Mouse Obese Gene and its Human Homologue" *Nature* 372: 425-432 (1994).
Abu-Elheiga et al. "Continuous Fatty Acid Oxidation and Reduced Fat Storage in Mice Lacking Acetyl-CoA Carboxylase 2" *Science* 291: 2613-2616 (2001).
Anderson et al. "Antidiabetic Agents: A New Class of Reversible Carnitine Palmitoyltransferase I Inhibitors" *J Med Chem* 38: 3448-3450 (1995).
Anderson et al. "Carnitine Palmitoyltransferase: A Viable Target for the Treatment of NIDDM" *Current Pharmaceutical Design* 4:1-15 (1998).
Banerjee et al. "Regulation of Fasted Blood Glucose by Resistin" *Science* 303: 1195-1198 (2004).
Deems et al. "Hypoglycemic Effects of a Novel Fatty Acid Oxidation Inhibitor in Rats and Monkeys" *Am J Physiol Regul Integr Comp Physiol* 274: 524-528 (1998).
Dobbins et al. "Prolonged Inhibition of Muscle Carnitine Palmitoyltransferase-1 Promotes Intramyocellular Lipid Accumulation and Insulin Resistance in Rats" *Diabetes* 50:123-130 (2001).
Gao et al. "Effect of the Anorectic Fatty Acid Synthase Inhibitor C75 on Neuronal Activity in the Hypothalamus and Brainstem" *PNAS* 100(10): 5628-5633 (2003).
International Search Report for International application No. PCT/US04/04344 completed on Nov. 3, 2005.
Kanamaru et al. "Emeriamine: A New Inhibitor of Long Chain Fatty Acid Oxidation and Its Antidiabetic Activity" *Novel Microbial Products for Medicine and Agriculture* Demain et al., editors, pp. 135-144 (1989).
Kim et al. "Expression of FAS within Hypothalamic Neurons: A Model for Decreased Food Intake After C75 Treatment" *Am J Physical Endocrinol Metab* 283:E867-E879 (2002).
Kong et al. "Palmitate-Induced Cardiac Apoptosis is mediated Through CPT-1 But Not Influenced by Glucose and Insulin" *Am J Physiology—Heart and Circ Physiol* 282: 717-725 (2002).
Kumar et al. "Differential Effects of a Centrally Acting Fatty Acid Synthase Inhibitor in Lean and Obese Mice" *PNAS* 99(4): 1921-1925 (2002).
Loftus et al. "Reduced Food Intake and Body Weight in Mice Treated with Fatty Acid Synthase Inhibitors" *Science* 288: 2379-2381 (2379-2381 (2000).
Morgan et al. "Central Effects of Oleic Acid on Glucose Production are Nutritionally Regulated" *Keystone Symposium*, Jan. 21-26, 2003 Keystone, Colorado (2003).
Obici et al. "Identification of a biochemical Link Between Energy Intake and Energy Expenditure" *The Journal of Clinical Investigation* 109(12): 1599-1605 (2002).
Obici et al. "Inhibition of Hypothalamic Carnitine Palmitoyltransferase I (CPT-1) Inhibits glucose Production and Food Intake" *Keystone Symposium*, Jan. 10-16, 2002 Keystone, Colorado (2002).
Obici et al. "Inhibition of Hypothalamic Carnitine Palmitoyltransferase-1 Decreases Food Intake and Glucose Production" *Nature Medicine* 9(6): 756-761 (2003).
Obici et al. "Central Administration of Oleic Acid Inhibits Glucose Production and Food Intake" *Diabetes* 51: 271-275 (2002).

Obici et al. "Decreasing Hypothalamic Insulin Receptors Causes Hyperphagia and Insulin Resistance in Rats" *Nature Neuroscience* 5(6): 566-572 (2002).

Obici et al. "Hypothalamic Insulin Signaling is Required for Inhibition of Glucose Production" *Nature Medicine* 8(12): 1376-1382 (2002).

Portilla et al. "Etomoxir-Induced PPARα-modulated Enzymes Protect During Acute Renal Failure" *Am J Phisiol Renal Phisiol* 278: F667-F675 (2000).

Ratheiser et al. "Inhibition by Etomoxir of Carnitine Palmitoyltransferase I Reduces hepatic Glucose Production and Plasma Lipids in Non-Insulin-Dependent Diabetes Mellitus" *Metabolism* 40(11): 1185-1190 (1991).

Rosetti "Food for Thought: Obesity, Diabetes May Be All in the Head" *HUM-MOLGEN News Alert* <http://www.hum-molgen.de/NewsGen/o5-2003/msg28.html> accessed on Nov. 9, 2003, 1 page (May 19, 2003).

Rossetti et al. "A Tale of Fat and Sugar" *Keystone Symposium*, Jan. 10-16, 2002 Keystone, Colorado (2002).

Rossetti et al. "Novel Mechanisms Linking Insulin Resistance to Obesity" *Keystone Symposium* Jan. 21-26, 2003 Keystone, Colorado (2003).

Shimokawa et al. "Effect of a Fatty Acid Synthase Inhibitor on Food Intake and Expression of Hypothalamic Neuropeptides" *PNAS* 99(1): 66-71 (2002).

Wolf "Possible New Therapeutic Approach in Diabetes Mellitus by Inhibition of Carnitine Palmitoyltransferase 1 (CPT1)" *Hormone and Metabolic Research Supplement Series* vol. 26 pp. 62-67 (1989).

\* cited by examiner

SEQUENCE LISTING

```
<160> NUMBER OF SEQ ID NOS: 18

<210> SEQ ID NO 1
<211> LENGTH: 50
<212> TYPE: RNA
<213> ORGANISM: Artificial
<220> FEATURE:
<223> OTHER INFORMATION: Inhibitory nucleic acid ribozyme sequence

<400> SEQUENCE: 1
acagcacgcc gcucugauga guccgugagg acgaaaccac guucuucguc         50

<210> SEQ ID NO 2
<211> LENGTH: 51
<212> TYPE: DNA
<213> ORGANISM: Artificial
<220> FEATURE:
<223> OTHER INFORMATION: Synthetic oligonucleotide comprising inhibitory
      nucleic acid ribozyme sequence

<400> SEQUENCE: 2
ctgtaccaaa gagctgatga gtccgtgagg acgaaacgcc gctcacaatg a        51

<210> SEQ ID NO 3
<211> LENGTH: 51
<212> TYPE: DNA
<213> ORGANISM: Artificial
```

```
<220> FEATURE:
<223> OTHER INFORMATION: Synthetic oligonucleotide comprising inhibitory
      nucleic acid ribozyme sequence

<400> SEQUENCE: 3
cattgtgagc ggcgtttcgt cctcacggac tcatcagctc tttggtacag a           51

<210> SEQ ID NO 4
<211> LENGTH: 50
<212> TYPE: DNA
<213> ORGANISM: Artificial
<220> FEATURE:
<223> OTHER INFORMATION: Control ribozyme sequence

<400> SEQUENCE: 4
ggagcctcga gatctgatga gtccgtgagg acgaaactgt gagcgtttgg              50

<210> SEQ ID NO 5
<211> LENGTH: 25
<212> TYPE: DNA
<213> ORGANISM: Artificial
<220> FEATURE:
<223> OTHER INFORMATION: PCR primer

<400> SEQUENCE: 5
ctccgagctc agtgaggacc taaag                                         25

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
caaataccac tgcaatttgt g                                             21

<210> SEQ ID NO 7
<211> LENGTH: 26
<212> TYPE: DNA
<213> ORGANISM: Artificial
<220> FEATURE:
<223> OTHER INFORMATION: PCR primer

<400> SEQUENCE: 7
ccagactgca gaaatacctg gtgctc                                        26

<210> SEQ ID NO 8
<211> LENGTH: 27
<212> TYPE: DNA
<213> ORGANISM: Artificial
<220> FEATURE:
<223> OTHER INFORMATION: PCR primer

<400> SEQUENCE: 8
gttctgacgt gcttctgccc actctac                                       27

<210> SEQ ID NO 9
<211> LENGTH: 23
<212> TYPE: DNA
<213> ORGANISM: Artificial
<220> FEATURE:
<223> OTHER INFORMATION: PCR primer

<400> SEQUENCE: 9
gccatgatgc taggtaacaa acg                                           23
```

<210> SEQ ID NO 10
<211> LENGTH: 23
<212> TYPE: DNA
<213> ORGANISM: Artificial
<220> FEATURE:
<223> OTHER INFORMATION: PCR primer

<400> SEQUENCE: 10
gtttcatttc ccatcaccac atg                                              23

<210> SEQ ID NO 11
<211> LENGTH: 19
<212> TYPE: DNA
<213> ORGANISM: Artificial
<220> FEATURE:
<223> OTHER INFORMATION: PCR primer

<400> SEQUENCE: 11
ccaggcaacg gagatgaac                                                   19

<210> SEQ ID NO 12
<211> LENGTH: 19
<212> TYPE: DNA
<213> ORGANISM: Artificial
<220> FEATURE:
<223> OTHER INFORMATION: PCR primer

<400> SEQUENCE: 12
tcactggccc ttcttgtgc                                                   19

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
gccatgctga ctgcaatgtt                                                  20

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
tggctaggtg cgactacaga                                                  20

<210> SEQ ID NO 15
<211> LENGTH: 22
<212> TYPE: DNA
<213> ORGANISM: Artificial
<220> FEATURE:
<223> OTHER INFORMATION: PCR primer

<400> SEQUENCE: 15
tgagaccttc aacaccccag cc                                               22

<210> SEQ ID NO 16
<211> LENGTH: 22
<212> TYPE: DNA
<213> ORGANISM: Artificial
<220> FEATURE:

```
<223> OTHER INFORMATION: PCR primer

<400> SEQUENCE: 16
gagtacttgc gctcaggagg ag                                            22

<210> SEQ ID NO 17
<211> LENGTH: 50
<212> TYPE: RNA
<213> ORGANISM: Artificial
<220> FEATURE:
<223> OTHER INFORMATION: Ribozyme transcript sequence

<400> SEQUENCE: 17
cuguaccaaa gagcuguaga guccgugagg acgaaacgcc gcucacaaug              50

<210> SEQ ID NO 18
<211> LENGTH: 29
<212> TYPE: RNA
<213> ORGANISM: Rattus norvegicus

<400> SEQUENCE: 18
cauugugagc ggcguccucu uugguacag                                     29
```

REGULATION OF FOOD INTAKE BY MODULATION OF LONG-CHAIN FATTY ACYL-COA LEVELS IN THE HYPOTHALAMUS

CROSS-REFERENCE TO RELATED APPLICATION

This application is a 35 U.S.C. §371 national phase application of International Application Serial No. PCT/US2004/004344, filed on Feb. 12, 2004, which claims the benefit of U.S. Provisional Application No. 60/447,138, filed Feb. 13, 2003, the disclosures of which are incorporated herein by reference in their entireties.

STATEMENT REGARDING FEDERALLY SPONSORED RESEARCH OR DEVELOPMENT

This invention was supported by NIH Grant Nos. DK 48321, DK 45024, DK 20541, R01-45024 and R01-4821. As such, the U.S. Government has rights in the invention.

BACKGROUND (1) Field of the Invention

The present invention generally relates to methods for regulating food intake and glucose production. More specifically, the invention relates to regulation of food intake and glucose production by manipulating lipid metabolism in the hypothalamus.

(2) Description of the Related Art

REFERENCES CITED

Ahima, R. S., Prabakaran, D., Mantzoros, C., Qu, D., Maratos-Flier, E., & Flier, J. S. Role of Leptin in the Neuroendocrine Response to Fasting. Nature 382, 250-252 (1996).

Air, E. L., et al. Small Molecule Insulin Mimetics Reduce Food Intake and Body Weight and Prevent Development of Obesity. Nat. Med. 8, 179-83 (2002).

Ausman, L. M., Rasmussen, K. M., and Gallina, D. L. Am. J. Physiol 241, R316-R321 (1981).

Barzilai, N., Wang, J., Massilon, D., Vuguin, P., Hawkins, M., and Rossetti, L. J. Clin. Invest 100, 3105-3110 (1997).

Berthoud, H. R. and Jeanrenaud, B. Endocrinology 105, 146-151 (1979).

Birikh, K. R., Heaton, P. A. & Eckstein, F. the Structure, Function and Application of the Hammerhead Ribozyme. Eur. J. Biochem. 245, 1-16 (1997).

Blazquez, C., Sanchez, C., Daza, A., Galve-Roperh, I. & Guzman, M. the Stimulation of Ketogenesis by Cannabinoids in Cultured Astrocytes Defines Carnitine Palmitoyltransferase I as a New Ceramide-activated Enzyme. J. Neurochem. 72, 1759-1768 (1999).

Boden, G., Chen, X., Ruiz, J., White, J. V., and Rossetti, L. J. Clin. Invest 93, 2438-2446 (1994).

Boussif, O. et al. A Versatile Vector for Gene and Oligonucleotide Transfer into Cells in Culture and in Vivo: Polyethylenimine. Proc. Natl. Acad. Sci. USA 92, 7297-7301 (1995).

Brief, D. J. and Davis, J. D. Brain Res. Bull. 12, 571-575 (1984).

Bruning, J. C., et al. Role of Brain Insulin Receptor in Control of Body Weight and Reproduction. Science 289, 2122-25 (2000).

Cinti, S., Frederich, R. C., Zingaretti, M. C., De Matteis, R., Flier, J. S., and Lowell, B. B. Endocrinology 138, 797-804 (1997).

Clore, 3. N., Helm, S. T., and Blackard, W. G. J. Clin. Invest 96, 1967-1972 (1995).

Combs, T. P., Berg, A. H., Obici, S., Scherer, P. E., and Rossetti, L. J. Clin. Invest 108, 1875-1881 (2001).

Coleman, D. L. Diabetologia 14, 141-148 (1978).

Coleman, D. L. Science 203, 663-665 (1979).

Di Marzo, V., et al. Leptin-regulated Endocannabinoids Are Involved in Maintaining Food Intake. Nature 410, 822-825 (2001).

Esser, V., Britton, C. H., Weis, B. C., Foster, D. W. & McGarry, J. D. Cloning, Sequencing, and Expression of a cDNA Encoding Rat Liver Carnitine Palmitoyltransferase I. Direct Evidence That a Single Polypeptide Is Involved in Inhibitor Interaction and Catalytic Function. J. Biol. Chem. 268, 5817-5822 (1993).

Flegal, K. M., Carroll, M. D., Ogden, C. L., and Johnson, C. L. JAMA 288, 1723-1727 (2002).

Frederich, R. C., Hamann, A., Anderson, S., Lollmann, B., Lowell, B. B., and Flier, J. S. Nat. Med. 1, 1311-1314 (1995).

Friedman, J. M. Obesity in the New Millennium. Nature 404, 632-634 (2000).

Friedman, J. M. Science 299, 856-858 (2003).

Giaccari, A. and Rossetti, L. J. Chromatogr. 497, 69-78 (1989).

Giaccari, A. and Rossetti, L. J. Clin. Invest 89, 3645 (1992).

Goto M., Spitzer 3.3. Fatty Acids Profiles of Various Lipids in the Cerebrospinal Fluid. Proc. Exp. Biol. Med. 136, 1294-1296 (1971).

Goula, D. et al. Size, Diffusibility and Transfection Performance of Linear PEI/DNA Complexes in the Mouse Central Nervous System. Gene Ther. 5, 712-717 (1998).

Halaas, J. L., Boozer, C., Blair-West, J., Fidahusein, N., Denton, D. A., and Friedman, J. M. Proc. Natl. Acad. Sci. U.S.A 94, 8878-8883 (1997).

Hall, J. E., Brands, M. W., Zappe, D. H., Dixon, W. N., Mizelle, H. L., Reinhart, G. A., and Hildebrandt, D. A. Hypertension 25, 994-1002 (1995).

Hawkins, M., et al. Diabetes 51, 2179-2189 (2002).

Hill, J. O. & Peters, J. C. Environmental Contributions to Obesity. Science 280,1371 (1998).

Kopelman, P. G. & Hitman, G. A. Diabetes. Exploding type H. Lancet 352, SIV5 (1998).

Kraegen, E. W., Clark, P. W., Jenkins, A. B., Daley, E. A., Chisholm, D. J., and Storlien, L. H. Diabetes 40, 1397-1403 (1991).

Inoue, S. and Bray, G. A. Endocrinology 100, 108-114 (1977).

Kahn, B. B. and Flier, J. S. J. Clin. Invest 106, 473-481 (2000).

Kersten, S. EMBO Rep. 2, 282-286 (2001).

Liu, et. al. Intracerebroventricular (ICV) Leptin Regulates Hepatic but Not Peripheral Glucose Fluxes. J. Biol. Chem. 273, 31160 (1998).

Loftus, T. M., Jarkowsky, D. E., Frehynot, G. L., Towsend, C. A., Ronnet, G. V., Lane M. D., Kuhajda, F. P. Reduced Food Intake and Body Weight in Mice Treated with Fatty Acid Synthase Inhibitors. Science 288, 2379 (2000).

Lunzer, M. A., Manning, J. A., & Ockner, R. K. Inhibition of Rat Liver Acetyl-CoA Carboxylase by Long-chain Acyl CoA and Fatty Acid. J. Biol. Chem. 252, 5283 (1977).

Makimura, H., Mizuno, T. M., Yang, X. J., Silverstein, J., Beasley, J., & Mobbs, C. V. Cerulenin Mimics Effects of Leptin on Metabolic Rate, Food Intake, and Body Weight Independent of the Melanocortin System, but Unlike Leptin, Cerulenin Fails to Block Neuroendocrine Effects of Fasting. Diabetes 50, 733-739 (2001).

Massillon, D., Chen, W., Barzilai, N., Prus-Wertheimer, D., Hawkins, M., Liu, R., Taub, R., and Miller, J. C., Gnaedinger, J. M., and Rapoport, S. I. J. Neurochem. 49, 1507-1514 (1987).

Massillon, D., Barzilai, N., Chen, W., Hu, M., and Rossetti, L. J. Biol. Chem. 271, 9871-9874 (1996).

Massillon, D., Barzilai, N., Hawkins, M., Prus-Wertheimer, D., and Rossetti, L. Diabetes 46, 153-157 (1997).

McGarry, G. D., Mannaert, G. P., Foster, D. W. A Possible Role for Malonyl-CoA in the Regulation of Hepatic Fatty Acid Oxidation and Ketogenesis. J. Clin. Invest. 60, 265-270 (1977).

Miller, J. C., Gnaedinger, J. M., Rapaport, S. I. Utilization of Plasma Fatty Acid in Rat Brain: Distribution of [$^{14}$C] Palmitate Between Oxidative and Synthetic Pathways. J. Neurochem. 49, 1507-1514 (1987).

Morgan, K., Obici, S., Feng, Z., & Rossetti, L. Central Effects of Oleic Acid on Glucose Production Are Nutritionally Regulated. Keystone Symposia Abstract Book, Keystone, Colo., Jan. 10-16, 2002 (2002).

Neel, J. V. Nutr. Rev. 57, S2-S9 (1999).

NHLBI (National Heart, Lung, and Blood Institute) Obesity Education Initiative. The Practical Guide—Identification, Evaluation and Treatment of Overweight and Obesity in Adults. NIH Publication No. 004084 (2000). Obtainable at http://www.nhlbi.nih.gov/guidelines/obesity/prctgd_b-.pdf.

Obici, S., Feng, Z., Tan, J., Liu, L., Karkanias, G.& Rossetti, L. Central Melanocortin Receptors Regulate Insulin Action. J. Clin. Invest. 108, 1079-1085 (2001).

Obici, S., Feng, Z., Morgan, K., Stein, D., Karkanias, G. & Rossetti, L. Central Administration of Oleic Acid Inhibits Glucose Production and Food Intake. Diabetes 51, 271-275 (2002a).

Obici, S., Feng, Z., Karkanias, G., Baskin, D. G., and Rossetti, L. Decreasing Hypothalamic Insulin Receptors Causes Hyperphagia and Insulin Resistance in Rats. Nat. Neurosci. 5, 566-572 (2002b).

Obici, S., Feng, Z., Morgan, K., Conti, R., Arduini, A., & Rossetti, L. Inhibition of Hypothalamic Carnitine Palmitoyltransferase I (CPT-1) Inhibits Glucose Production and Food Intake. Keystone Symposia Abstract Book, Keystone, Colo., Jan. 10-16, 2002 (2002c).

Obici, S., Wang, J., Chowdury, R., Feng, Z., Siddhanta, U., Morgan, K., and Rossetti, L. J. Clin. Invest 109, 1599-1605 (2002d).

Obici, S., Zhang, B. B., Karkanias, G., and Rossetti, L. Nat. Med. 8, 1376-1382 (2002e).

Obici, S., Feng, Z., Karkanias, G., Baskin, D. G., and Rossetti, L. Nat. Neurosci. 5, 566-572 (2002f).

Obici, S., Feng, Z., Arduini, A., Conti, R., and Rossetti, L. Nat. Med. 9, 756-761 (2003).

Ogden, C. L., Flegal, K. M., Carroll, M. D., and Johnson, C. L. JAMA 288, 1728-1732 (2002).

Pagliassotti, M. J., Gayles, E. C., and Hill, J. O. Ann. N.Y. Acad. Sci. 827, 431-448 (1997).

Palkovits M. Isolated Removal of Hypothalamic or Other Brain Nuclei of the Rat. Brain Research. 59, 449-450 (1973).

Paxinos, G., and Watson, C. The Rat Brain in Stereotaxic Coordinates. 3rd Edition, Academic Press, California, USA (1997).

Pitha, J., Gerloczy, A., and Olivi, A. J. Pharm. Sci. 83, 833-837 (1994).

Porte, D., Jr., Seeley, R. J., Woods, S. C., Baskin, D. G., Figlewicz, D. P., and Schwartz, M. W. Diabetologia 41, 863-881 (1998).

Qi, K., Hall, M., and Deckelbaum, R. J. Curr. Opin. Clin. Nutr. Metab Care 5, 133-138 (2002).

Rajala, M. W., Obici, S., Scherer, P. E., and Rossetti, L. J. Clin. Invest 111, 225-230 (2003).

Rapoport, S. I. Lipids 31 Suppl, S97-101 (1996).

Rapoport, S. I. J. Mol. Neurosci. 16, 243-261 (2001).

Ravussin, E. and Gautier, J. F. Int. J. Obes. Relat Metab Disord. 23 Suppl 1, 37-41 (1999).

Rebrin, K., Steil, G. M., Getty, L., and Bergman, R. N. Diabetes 44, 1038-1045 (1995).

Roden, M., Price, T. B., Perseghin, G., Petersen, K. F., Rothman, D. L., Cline, G. W., and Romsos, D. R., Miller, E. R., and Leveille, G. A. Proc. Soc. Exp. Biol. Med. 157, 528-530 (1978).

Rossetti, L., Giaccari, A., Barzilai, N., Howard, K., Sebel, G., and Hu, M. J. Clin. Invest 92, 1126-1134 (1993).

Rossetti, L., Barzilai, N., Chen, W., Harris, T., Yang, D., and Rogler, C. E. J. Biol. Chem. 271, 203-208 (1996).

Rossetti, L. J. Biol. Chem. 273, 228-234 (1998).

Schemmel, R., Mickelsen, O., and Gill, J. L. J. Nutr. 100, 1041-1048 (1970).

Schwartz, M. W., Seeley, R. J., Campfield, L. A., Burn, P., and Baskiin, D. G. J. Clin. Invest 98, 1101-1106 (1996a).

Schwartz, M. W., Baskin, D. G., Bukowski, T. R., Kuijper, J. L., Foster, D., Lasser, G., Prunkard, D. E., Porte, D., Jr., Woods, S. C., Seeley, R. J., and Weigle, D. S. Diabetes 45, 531-535 (1996b).

Schwartz, M. W., Woods, S. C., Porte, D. Jr., Seeley, R. J., Baskin, D. G. Central Nervous System Control of Food Intake. Nature 404, 661-671 (2000).

Sclafani, A. and Springer, D. Physiol Behav. 17, 461-471 (1976).

Shimazu, T., Matsushita, H., and Ishikawa, K. Brain Res. 144, 343-352 (1978).

Shimazu, T. Nutrition 12, 65-66 (1996).

Shimokawa, T., Kumar, M. V., & Lane, M. D. Effect of a Fatty Acid Synthase Inhibitor on Food Intake and Expression of Hypothalamic Neuropeptides. Proc. Natl. Acad. Sci. USA 99, 66-71 (2002).

Shimomura, I., Hammer, R. E., Ikemoto, S., Brown, M. S., and Goldstein, J. L. Nature 401, 73-76 (1999).

Shulman, G. I. J. Clin. Invest 97, 2859-2865 (1996).

Spiegelman, B. M. and Flier, J. S. Cell 104, 531-543 (2001).

Thupari, J. N., Landree, L. E., Ronnett, G. V., and Kuhajda, F. P. Proc. Natl. Acad. Sci. U.S.A 99, 9498-9502 (2002).

Wang, Q., Bing, C., Al Barazanji, K., Mossakowaska, D. E., Wang, X. M., McBay, D. L., Neville, W. A., Taddayon, M., Pickavance, L., Dryden, S., Thomas, M. E., McHale, M. T., Gloyer, I. S., Wilson, S., Buckingham, R., Arch, J. R., Trayhurn, P., and Williams, G. Diabetes 46, 335-341 (1997).

Wang, J., Liu, R., Hawkins, M., Barzilai, N., Rossetti, L. A Nutrient-sensing Pathway Regulates Leptin Gene Expression in Muscle and Fat. Nature 393, 684-688 (1998).

Wang, J., Obici, S., Morgan, K., Barzilai, N., Feng, Z., and Rossetti, L. Diabetes 50, 2786-2791 (2001).

West, D. B., Boozer, C. N., Moody, D. L., and Atkinson, R. L. Am. J. Physiol 262, R1025-R1032 (1992).

West, D. B., Waguespack, J., and McCollister, S. Am. J. Physiol 268, R658-R665 (1995).

Widdowson, P. S., Upton, R., Buckingham, R., Arch, J., and Williams, G. Diabetes 46, 1782-1785 (1997).

Woods, S. C., Lotter, E. C., McKay, D. L., & Porte, D. Jr. Chronic Intracerebroventricular Infusion of Insulin Reduces Food Intake and Body Weight of Baboons. Nature. 282, 503-5 (1979).

Woods, S. C., Seeley, R. J., Porte, D., Jr., and Schwartz, M. W. Science 280, 1378-1383 (1998).

Yaksh, T. L., Jang, J. D., Nishiuchi, Y., Braun, K. P., Ro, S. G., and Goodman, M. Life Sci. 48, 623-633 (1991).

Zammit, V. A. Regulation of Ketone Body Metabolism. A Cellular Perspective. Diabetes Rev. 2, 132-155 (1994).

Zhang, Y., Proenca, R., Maffei, M., Barone, M., Leopold, L., and Friedman, J. M. Nature 372, 425-432 (1994).

Complex metabolic diseases such as obesity and type 2 diabetes mellitus are the result of multiple interactions between genes and environment (Hill & Peters, 1998; Kopelman & Hitman, 1998). Hypothalamic centers sense the availability of peripheral nutrients partly via redundant nutrient-induced peripheral signals such as leptin and insulin (Woods et al., 2000; Bruning et al., 2000; Friedman, 2000; Air et al., 2002; Schwartz et al., 2000; Ahima et al., 1996; Wang et al., 1998) and via direct metabolic signaling, e.g., by addition of oleic acid to the hypothalamus (Loftus et al., 2000; Obici et al., 2002a; Makimura et al., 2001; Shimokawa et al., 2002). In this regard, lipid metabolism in selective hypothalamic neurons has been postulated to be a primary biochemical sensor for nutrient availability, which in turn exerts a negative feedback on food intake (Loftus et al., 2000; Makimura et al., 2001; Obici et al., 2002a; Obici et al., 2002c; Shimokawa et al., 2002) and endogenous glucose production (GP) (Obici et al., 2002a). This theory has not heretofore been validated, and there is some evidence that this negative feedback is ineffective in overfed animals (Morgan et al., 2002).

Thus, there is a need for further elucidation of central mechanisms for hypothalamic metabolic signaling. The present invention satisfies that need.

SUMMARY OF THE INVENTION

Accordingly, the inventors have discovered that food intake and glucose production can be modulated in mammals by modulating long-chain fatty acyl-Co-A (LC-CoA) levels in the hypothalamus of the mammal.

Thus, the invention is directed to methods of reducing food intake and glucose production in a mammal. The methods comprise increasing LC-CoA levels in the hypothalamus. In these methods, the mammal preferably has at least one condition selected from the group consisting of obesity, type 2 diabetes, leptin resistance, insulin resistance, gonadotropin deficiency, amenorrhea, and polycystic ovary syndrome.

In other embodiments, the invention is directed to methods of increasing food intake and glucose production in a mammal. The methods comprise decreasing LC-CoA levels in the hypothalamus of the mammal. In these methods the mammal is preferably suffering from a condition characterized by insufficient food intake or glucose production.

The invention is additionally directed to methods of restoring hepatic autoregulation in a mammal with inadequate hepatic autoregulation. The methods comprise increasing long-chain fatty acyl-Co-A (LC-CoA) levels in the hypothalamus of the mammal.

In additional embodiments, the invention is directed to methods of reducing food intake and glucose production in a mammal. The methods comprise stimulating an efferent hepatic vagus nerve fiber.

The invention is also directed to methods of restoring hepatic autoregulation in a mammal with inadequate hepatic autoregulation. The methods comprise stimulating an efferent hepatic vagus nerve fiber.

DETAILED DESCRIPTION OF THE INVENTION

Figure 1:
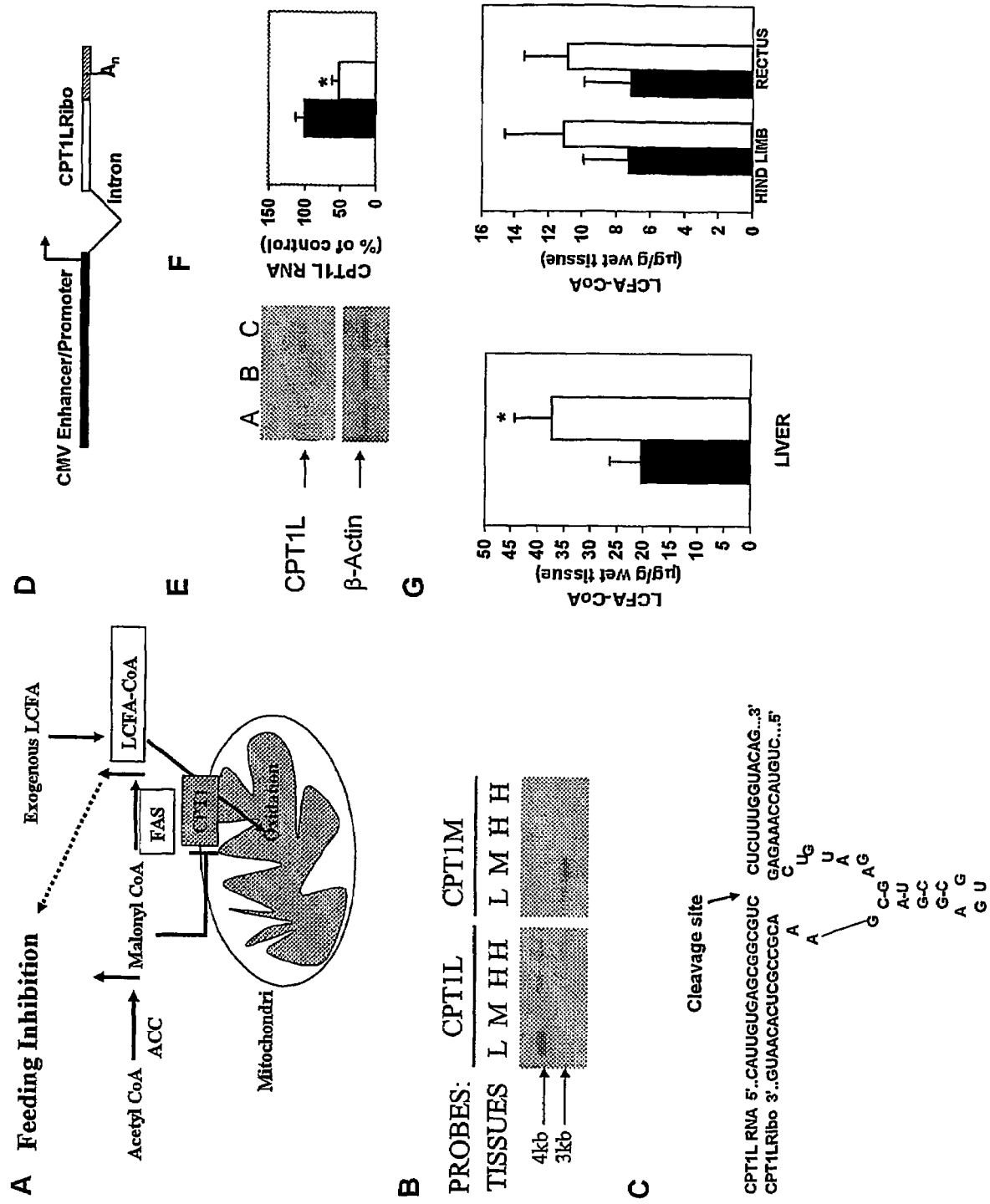
FIG. 1 shows graphics, northern blots, and graphs describing characteristics of lipid metabolism and experiments related to the inhibition of hypothalamic carnitine palmitoyl transferase 1 (CPT1). Panel A shows a proposed model for the role of CPT1 in the hypothalamic regulation of food intake. Potent anorexic drugs such as fatty acid synthase (FAS) inhibitors increase the levels of malonyl-CoA, which is derived from the carboxylation of acetyl-CoA by the enzyme acetyl-CoA carboxylase (ACC). High levels of malonyl-CoA in turn inhibit CPT1-dependent oxidation of long-chain fatty acyl-CoAs (LC-CoAs). Similarly, the ICV administration of exogenous fatty acids (LCFA) directly increases the cellular levels of LC-CoA. In either case the resulting increase in intracellular LC-CoA concentration leads to inhibition of feeding behavior. Panel B shows a northern blot analysis of CPT1 expression in whole rat hypothalamus. LEFT: A probe specific for the liver isoform of CPT1 (CPT1L) detected a ~4.3 Kb band in the liver (L) and in hypothalamus (H), but not in hind limb muscle (M). RIGHT: Hybridization with a muscle-specific CPT1 probe (CPT1M) detected a ~3 Kb band in liver (L) and muscle (M), but not in hypothalamus. Each lane contained 1.5 μg of mRNA. Panel C shows the design of a ribozyme selective for CPT1L mRNA. CPT1L-Ribo transcript (lower sequence, SEQ ID NO: 17) contains a central sequence with a stem-loop structure typical of a hammerhead ribozyme, flanked by sequences that hybridize to the target CPT1L mRNA (upper sequence, SEQ ID NO: 18). The arrow marks the predicted cleavage site Panel D shows the construction of a CPT1L-Ribo plasmid. The CPT1L-Ribo fragment was cloned into a mammalian expression vector (pTarget) under the control of a CMV promoter and immediately downstream of an intron cassette and upstream of a SV40 polyadenylation signal ($A_n$). Panel E shows that AtT20 cells expressing CPT1L-Ribo have decreased levels of CPT1 L mRNA. About 200 stable clones were selected for neomycin resistance and analyzed by Northern blot. Each lane contained 1.0 μg of polyadenylated RNA from AtT20 transfected with vector alone (Lane A), CPT1L-Ribo plasmid (Lane B), or non-transfected (Lane C). Blots were hybridized with CPT1L probe (Upper panel) or with β-actin (lower panel). Panel F shows the quantification of AtT20 northern blots. Cells expressing CPT1L-Ribo (■) contain ~50% less CPT1L mRNA than control cells transfected with vector alone (□). Data are expressed as % of control after normalization with β-actin expression. Panel G shows that systemic administration of CPT1 inhibitors increases intracellular levels of LC-CoA. Levels of LC-CoAs were measured by HPLC in liver and skeletal muscle tissues of rats infused IV with vehicle (■) or CPT1 inhibitors (□).

The present invention is based in part on the discovery that food intake and glucose production in a mammal can be modulated by modulating long-chain fatty acyl-Co-A (LC-CoA) levels in the hypothalamus of the mammal. See Examples 1 and 2.

Thus, in some embodiments, the present invention is directed to methods of reducing food intake and glucose production in a mammal. The methods comprise increasing LC-CoA levels in the hypothalamus of the mammal.

As used herein, LC-CoA are saturated or unsaturated C14-C22 esters of coenzyme A. In preferred embodiments, the LC-CoA is C16 or C18 and is monounsaturated.

The skilled artisan would understand that these methods would be effective in treating conditions such as obesity, type 2 diabetes mellitus and insulin resistance. Additionally, the effects of CPT1 inhibition on NPY and agouti-related protein (AgRP) levels in the arcuate nuclei establish that these methods would likely be an effective treatment for leptin resistance and for the effects of insulin and leptin resistance, such as controlling LH surge, amenorrhea and other reproductive dysfunctions related to gonadotropin deficiency, including polycystic ovary syndrome.

In some aspects of these methods, the LC-CoA is increased by decreasing the activity of an LC-CoA-decreasing molecule in the hypothalamus. As used herein, an LC-CoA-decreasing molecule is a molecule affecting lipid metabolism that has the effect of inhibiting production or promoting metabolism of LC-CoA. Included are enzymes or carrier proteins, now known or later discovered, that drive lipid metabolism away from production of LC-CoA, or toward metabolism of LC-CoA. The enzymes include, but are not limited to, enzymes that directly metabolize LC-CoA. Non-limiting examples of enzymes included within these embodiments are carnitine palmitoyl transferase 1 (CPT1), malonyl-CoA decarboxylase, carnitine acylcarnitine translocase, acyl-CoA dehydrogenase, 2-enoyl-CoA hydratase, 3-hydroxyacyl-CoA dehydrogenase, 3-oxyacyl-CoA thiolase, and acyl-CoA hydrolase.

As used herein, "decreasing the activity" of a molecule means either reducing the action (e.g., enzyme activity or binding to a ligand such as LC-CoA) of a preexisting molecule as it relates to LC-CoA production or metabolism, or reducing the amount of such molecules, or combinations thereof. It should be understood that the amount of the molecules can be reduced by increasing the rate of degradation or removal of the molecule and/or reducing the biosynthesis of the molecule. Conversely, "increasing the activity" encompasses methods that increase the action of a preexisting molecule as it relates to LC-CoA production or metabolism, or increasing the amount of such molecules, or combinations thereof. The amount of a molecule can be increased by reducing the rate of degradation or removal of the molecule and/or increasing the biosynthesis of the molecule and/or adding the molecule.

Also included as LC-CoA-decreasing molecules are short interfering RNAs (siRNAs) or other molecules (e.g., cytokines and inhibitors) that directly or indirectly inhibit production of enzymes that promote production or buildup of LC-CoA. As is well known, siRNAs, cytokines, inhibitors and other molecules can have a strong effect in regulating the production or activity of an enzyme or carrier protein.

In some preferred embodiments, the LC-CoA-decreasing molecule is CPT1, since that enzyme is at an important rate-limiting step in β-oxidation of LC-CoA. Additionally, the form of CPT1 in the hypothalamus and liver, carnitine palmitoyl transferase-1, liver isoform (CPT1L), is known to be different from the form of CPT1 in the muscle (CPT1M), which allows the use of inhibitors of the CPT1L but not the CPT1M form, thus limiting the side effects caused by the method. The inventors have also already demonstrated the utility of decreasing the activity of hypothalamic CPT1L in the methods of the invention. See, e.g., Examples 1 and 2. However, the effectiveness of targeting CPT1L strongly indicates that inhibition of any other LC-CoA-decreasing molecule would be expected to also reduce food intake and glucose production.

In more preferred embodiments, the CPT1 is CPT1L, and the treatment selectively or specifically reduces activity of that variant and not CPT1M, in order to minimize side effects of inhibition of CPT1M.

In some embodiments, the activity of the LC-CoA-decreasing molecule is decreased by administering a pharmaceutical composition to the brain of the mammal. As used herein, a pharmaceutical composition is a composition of at least one small molecule capable of decreasing the activity of the LC-CoA-decreasing molecule, in a pharmaceutically acceptable excipient. As used herein, a "small molecule" is a molecule of less than about 2000 MW that is not an oligopeptide or oligonucleotide. An oligopeptide and oligonucleotide is an unbranched chain of at least two peptides or nucleotides, respectively. Examples of small molecules useful in these embodiments are inhibitors of any LC-CoA-decreasing molecule, including ST1326 and 2-tetradecylglydate (TDGA), known inhibitors of CPT1.

In these embodiments, the pharmaceutical composition is either directly administered to the brain such that the small molecule enters the hypothalamus (e.g., administration into the third cerebral ventricle (ICV)), or by administration of a composition where the small molecule is capable of crossing the blood-brain barrier. Here, the small molecule is capable of crossing the blood-brain barrier by itself, and/or with the aid of at least one excipient present in the pharmaceutical composition.

In other embodiments, the activity of the LC-CoA-decreasing molecule is decreased by administering an antibody or antibody fragment comprising an antibody binding site to the brain (e.g., ICV) of the mammal. In these embodiments, the antibody or antibody fragment is capable of binding to the LC-CoA-decreasing molecule to inhibit the activity of the molecule. Here, the antibodies or antibody fragments are not limited to any particular form (e.g., polyclonal, monoclonal, FAb fragments, etc.) or made by any particular method (e.g., stimulation and harvest of antibodies from an animal or hybridoma cells made from an animal, or production by recombinant methods such as phage or recombinant yeast or bacteria).

The activity of the LC-CoA-decreasing molecule can also be decreased by administration of an inhibitory nucleic acid or mimetic to the brain of the mammal. As used herein, a mimetic is an artificial compound, now known or later discovered, that behaves similarly to a nucleic acid by having the ability to base-pair with a complementary nucleic acid. Non-limiting examples of known mimetics include peptide nucleic acids and phosphorothionate mimetics.

Examples of inhibitory nucleic acids or mimetics include ribozymes, antisense compounds and siRNA, which bind to the target mRNA (antisense) or direct endogenous mechanisms to degrade the mRNA (siRNA), or cleave mRNA (ribozymes), preventing translation of the target protein. Another example of inhibitory nucleic acids or mimetics is aptamers, which bind to, and inhibit, the target molecule in a manner similar to an antibody or small molecule inhibitor.

In some preferred embodiments, the inhibitory nucleic acid or mimetic is a ribozyme (see Example 1, providing a rat CPT1L-specific ribozyme). Where the LC-CoA-decreasing molecule is human CPT1L, an example of a ribozyme for use in these methods comprises the sequence 5'-ACAGCACGC-CGCUCUGAUGAGUCCGUGAGGACGAAAC-CACGUUCUUCGUC-3' (SEQ ID NO:1), where the bolded sequence is the catalytic core of a hammerhead ribozyme.

The inhibitory nucleic acids are preferably administered to the brain of the mammal, most preferably into the third cerebral ventricle. Alternatively, a vector encoding the inhibitory nucleic acid can be administered, where the vector encodes the inhibitory nucleic acid operably linked to control elements such as promoters, enhancers and terminators such that the inhibitory nucleic acid is synthesized such that it becomes present in the hypothalamus. Methods for producing such vectors are well known in the art. Viral vectors (e.g., lentivirus or adenovirus vectors) are known to be particularly useful in these embodiments.

In other aspects of these methods, the LC-CoA is increased by increasing the activity of an LC-CoA-increasing molecule in the hypothalamus. As used herein, an LC-CoA-increasing molecule is a molecule affecting lipid metabolism that has the effect of promoting production or reducing metabolism of LC-CoA. Included are enzymes or carrier proteins, now known or later discovered, that drive lipid metabolism toward production of LC-CoA, or away from metabolism of LC-CoA. The enzymes include, but are not limited to, enzymes that directly produce LC-CoA. Non-limiting examples of enzymes included within these embodiments are acetyl-CoA carboxylase, fatty acid transporter molecule, acyl-CoA synthetase, carnitine palmitoyl transferase II, and acyl-CoA thioesterase.

In some embodiments of these methods, the activity of the LC-CoA-increasing molecule is increased by administering a pharmaceutical composition to the brain of the mammal, the pharmaceutical composition comprising a small molecule capable of stimulating production or activity of the LC-CoA-increasing molecule.

As with previous embodiments, the pharmaceutical composition is either directly administered to the brain such that the small molecule enters the hypothalamus (e.g., administration into the third cerebral ventricle (ICV)), or by administration of a composition where the small molecule is capable of crossing the blood-brain barrier.

The activity of the LC-CoA-increasing molecule can also be increased in these methods by administering the molecule, in a pharmaceutically acceptable carrier, to the mammal such that the molecule is able to enter the hypothalamus. In preferred embodiments, the molecule is administered directly to the brain of the mammal in the vicinity of the hypothalamus (e.g., into the third cerebral ventricle).

Alternatively, the activity of the LC-CoA-increasing molecule can be increased in these methods by administering a vector encoding the molecule, in a pharmaceutically acceptable carrier, to the mammal such that the vector is able to enter the hypothalamus and the molecule can be produced therefrom. As with previous embodiments, the portion of the vector encoding the molecule is preferably operably linked to control sequences directing production of the molecule from the vector in the hypothalamus.

In additional aspects of these methods, the LC-CoA is increased by directly administering LC-CoA to the brain of the mammal, preferably into the third cerebral ventricle.

The above methods are useful for decreasing food intake and glucose production in any mammal, including rodents and humans.

These methods are particularly useful for treatment of type 2 diabetes mellitus and obesity. Treatment of any degree of obesity is envisioned. Preferably, the mammal is at least 5% over normal body weight. In other embodiments, the mammal is at least 20% over normal body weight. As used herein, human normal body weight is defined as a BMI index 18.5-24.9 $Kg/meter^2$ (NHLBI, 2000). A BMI index of above 24.9 $kg/meter^2$ is considered obese herein.

These methods would be expected to decrease food intake by at least 5%, although decreases in food intake of at least 10%, 20%, 30%, or 40% would also not be unexpected.

The invention is additionally directed to methods of increasing food intake and glucose production in an mammal suffering from a condition characterized by insufficient food intake or glucose production. The methods comprise decreasing long-chain fatty acyl-Co-A (LC-CoA) levels in the hypothalamus of the mammal.

These methods are useful in any situation where it is desired that the mammal increase its food intake or glucose production. Examples of such situations are when the mammal is undergoing a treatment that causes insufficient food intake or glucose production, for example cancer chemotherapy, or when the mammal has an infection, such as a viral infection (e.g., HIV-1 infection) that causes insufficient food intake or glucose production. The methods are also effective in mammals that are hypoglycemic.

In some aspects of these embodiments, the LC-CoA levels are decreased by decreasing the activity of an LC-CoA-increasing molecule (e.g., acetyl-CoA carboxylase, fatty acid transporter molecule, acyl-CoA synthetase, carnitine palmitoyl transferase II, and acyl-CoA thioesterase) in the hypothalamus. As previously discussed, examples of ways that the activity of a molecule can be decreased are by (a) administering a pharmaceutical composition to the brain of the mammal, where the pharmaceutical composition comprises a small molecule capable of inhibiting the activity of the LC-CoA-decreasing molecule; (b) administering an antibody or antibody fragment comprising an antibody binding site to the brain of the mammal, where the antibody or antibody fragment is capable of binding to the LC-CoA-increasing molecule to inhibit the activity of the molecule; and/or (c) administering an inhibitory nucleic acid or mimetic (e.g., a ribozyme, an antisense compound, an aptamer or an iRNA) to the brain of the mammal.

In other aspects of these embodiments, the LC-CoA levels are decreased by increasing the activity of an LC-CoA-decreasing molecule (e.g., carnitine palmitoyl transferase 1 (CPT1), malonyl-CoA decarboxylase, carnitine acylcarnitine translocase, acyl-CoA dehydrogenase, 2-enoyl-CoA hydratase, 3-hydroxyacyl-CoA dehydrogenase, 3-oxyacyl-CoA thiolase, and acyl-CoA hydrolase) in the hypothalamus. Also as previously discussed, examples of ways that the activity of a molecule can be increased are by (a) administering a pharmaceutical composition to the brain of the mammal, the pharmaceutical composition comprising a small molecule capable of increasing activity of the LC-CoA-increasing molecule; (b) administering the molecule to the hypothalamus; and (c) administering a vector encoding the molecule to the hypothalamus.

These methods are useful for increasing food intake and glucose production for any mammal, in particular rodents or humans. In some embodiments, the mammal is at least 10% or 20% below normal body weight.

These methods would be expected to increase food intake in the mammal by at least 5%, 10%, 20%, 30% or 40%.

The inventors have also succeeded in discovering that hepatic autoregulation can be mediated by LC-CoA levels in the hypothalamus. See Example 4. Thus, in some embodiments, the invention is directed to methods of restoring hepatic autoregulation in a mammal with inadequate hepatic autoregulation. The methods comprise increasing LC-CoA levels in the hypothalamus of the mammal.

As used herein, "hepatic autoregulation" describes a phenomenon where, in the presence of basal insulin levels, increasing the circulating levels of free fatty acid via lipid infusions stimulates gluconeogenesis but does not alter endogenous glucose production because of a compensatory decrease in hepatic glycogenolysis. This phenomena can be dysfunctional in diabetics, contributing to high plasma glucose levels (See, e.g., Hawkins et al., 2002).

In these embodiments, LC-CoA levels are increased in the hypothalamus by the same methods as described for previous embodiments, e.g., by decreasing the activity of an LC-CoA-decreasing molecule in the hypothalamus, e.g., where the LC-CoA-decreasing molecule is CPT1, in particular CPT1L, for example by administering a pharmaceutical composition to the brain of the mammal, the pharmaceutical composition comprising a small molecule capable of decreasing the activity of the LC-CoA-decreasing molecule, by administering an antibody or antibody fragment comprising an antibody binding site to the brain of the mammal, wherein the antibody or antibody fragment is capable of binding to the LC-CoA-decreasing molecule to inhibit the activity of the molecule; by administering an inhibitory nucleic acid or mimetic (e.g., a ribozyme) to the brain of the mammal. LC-CoA levels in these embodiments can also be increased by increasing the activity of an LC-CoA-increasing molecule in the hypothalamus, as described above, or by directly administering LC-CoA to the brain. Also as in previous embodiments, these methods are useful for any mammal, for example a rodent or a human, in particular a diabetic mammal.

Additionally, the inventors have discovered that increases in hypothalamic LC-CoA causes reduction in food intake and glucose production through stimulation of efferent fibers of the hepatic branch of the vagus nerve. See Example 4. The skilled artisan would understand that reduced food intake and glucose production can be achieved by stimulating an efferent hepatic vagus nerve fiber.

Thus, the invention is also directed to methods of reducing food intake and glucose production in a mammal. The methods comprise stimulating an efferent hepatic vagus nerve fiber in the mammal. In these embodiments, the mammal has at least one condition selected from the group consisting of obesity, type 2 diabetes, leptin resistance, insulin resistance, gonadotropin deficiency, amenorrhea, and polycystic ovary syndrome.

The vagus nerve is also known in the art as the parasympathetic nervous system and its branches, and the cholinergic nerve. The efferent hepatic vagus nerve fibers can be stimulated by any means known in the art. Nonlimiting examples include: mechanical means such as a needle, ultrasound, or vibration; any electromagnetic radiation such as infrared, visible or ultraviolet light; heat, or any other energy source. In preferred embodiments, the vagus nerve is stimulated electrically, using for example a commercial vagus nerve stimulator such as the Cyberonics NCP®, or an electric probe. The efferent vagus nerve can be stimulated by stimulating the entire vagus nerve (i.e., both the afferent and efferent nerves), or by isolating efferent nerves and stimulating them directly. The latter method can be accomplished by separating the afferent from the efferent fibers in an area of the nerve where both types of fibers are present. Alternatively, the hepatic efferent fiber is stimulated where no afferent fibers are present, for example close to the liver. The efferent fibers can also be stimulated by stimulating the liver directly, e.g., electrically, thus stimulating the efferent fibers that serve that liver. The vagus nerve can also be cut and the distal end can be stimulated, thus only stimulating efferent vagus nerve fibers.

The amount of stimulation useful to inhibit an food intake and glucose production can be determined by the skilled artisan without undue experimentation. An example of electrical stimulation known to stimulate the vagus nerve is constant voltage stimuli of 1 to 5 V, at 2 ms and 1 Hz, for 10 min.

In related embodiments, the invention is directed to additional methods of restoring hepatic autoregulation in a mammal with inadequate hepatic autoregulation. The methods comprise stimulating an efferent hepatic vagus nerve fiber. The methods of stimulating the efferent hepatic vagus nerve fiber are precisely as described in the embodiments immediately above relating to the reduction of food intake and glucose production.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Inhibition of Hypothalamic Carnitine Palmitoyltransferase-1 Decreases Food Intake and Glucose Production Example Summary The enzyme carnitine palmitoyl transferase-1 regulates the entry of long-chain fatty acids in the mitochondria where they can undergo β-oxidation. In order to examine novel mechanism(s) by which central metabolism of lipids can modulate energy balance, we aimed to selectively reduce lipid oxidation in the hypothalamus. To this end, the activity of carnitine palmitoyl transferase-1 was diminished via administration of a ribozyme-containing plasmid designed to specifically decrease the expression of this enzyme or via infusion of pharmacological inhibitors of its activity in the third cerebral ventricle. Either genetic or biochemical inhibition of hypothalamic carnitine palmitoyl transferase-1 activity was sufficient to markedly diminish food intake and endogenous glucose production. These results indicate that changes in the rate of lipid oxidation in selective hypothalamic neurons can signal nutrient availability to the hypothalamus, which in turn modulates the exogenous and endogenous inputs of nutrients into the circulation.

Introduction

This example describes experimental results directed to the mechanism responsible for the lipid-dependent signal by examining the role of hypothalamic lipid oxidation. The enzyme, carnitine palmitoyl transferase-1 (CPT1), regulates the entry of long-chain fatty acids in the mitochondria where they can undergo β-oxidation (McGarry et al., 1977; Zammit, 1994). Two observations drove our attention to the possible role of hypothalamic CPT1: a) the suppressive effect of inhibitors of fatty acid synthase (FAS) on food intake requires increased levels of malonyl-CoA, a potent inhibitor of CPT-1 activity (Loftus et al., 2000) (FIG. 1a); and b) the suppressive effects of the long-chain fatty acid (LCFA) oleic acid delivered in the third cerebral ventricle (ICV) on food intake and on GP were not replicated by equimolar administration of octanoic acid, a short-chain fatty acid that does not require CPT1 for entry in the mitochondria (Obici et al., 2002a). Based on these previous findings we postulated that an increase in neuronal LC-CoA levels is a hypothalamic signal of nutrient availability. This increase could be generated by either the ICV administration of LCFAs (such as oleic acid) (Id.) or the inhibition of LC-CoA entry in the mitochondria due to increased levels of malonyl-CoA (Loftus et al., 2000). To test this hypothesis we asked whether a primary decrease in CPT-1 activity in the hypothalamus is sufficient to inhibit both feeding behavior and GP.

Results

Molecular and pharmacological approaches to CPT1 inhibition. To inhibit the entry of LC-CoAs in the mitochondria, we pursued pharmacological and molecular approaches. We first demonstrated that the prevalent form of CPT1 in the hypothalamus by northern analysis is the liver (CPT1L) rather than the muscle (CPT1M) isoform (FIG. 1b). We therefore designed a ribozyme (CPT1L-Ribo; FIG. 1c) that specifically cleaves CPT1L mRNA and introduced it into a mammalian expression vector (FIG. 1d). We then tested the ability of this construct to decrease CPT1L expression in stably transfected AtT20 cells (FIGS. 1e and 1f). We also demonstrated that the systemic infusion of CPT1 inhibitors could significantly increase the concentration of LC-CoAs in liver and skeletal muscle (FIG. 1g). Thus we validated the use of a CPT1L-Ribo to decrease CPT1 expression in mammalian cells and provided evidence that inhibition of CPT1 activity per se is sufficient to increase the tissue concentration of LC-CoAs.

Figure 2:
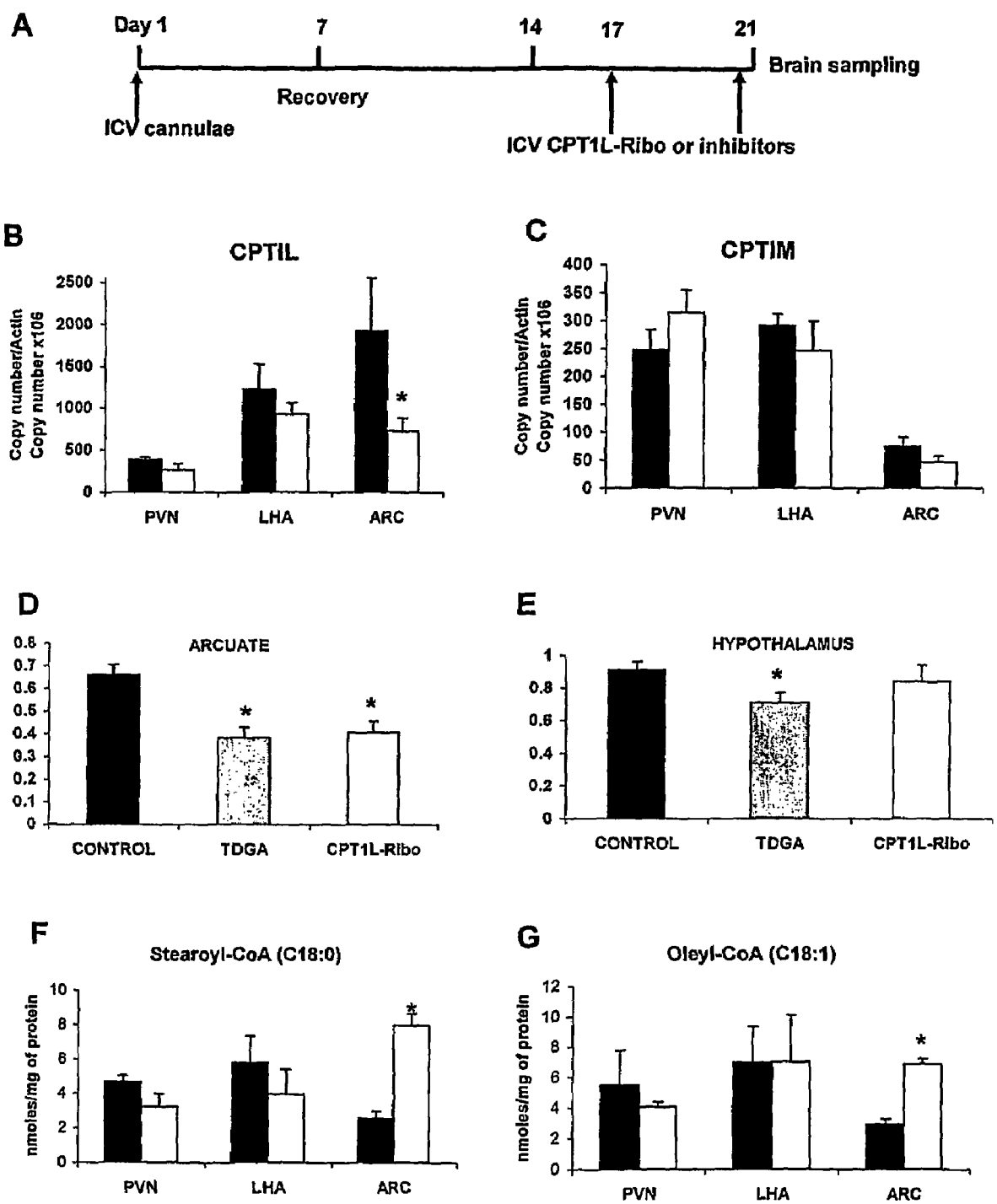
FIG. 2 shows graphs summarizing experimental results establishing that genetic or pharmacological inhibition of CPT1 in the arcuate nucleus reduces CPT1 activity and increases levels of LC-CoAs. Panel A shows a schematic representation of the experimental procedures. Surgical implantation of ICV cannulae was performed on day 1 (~3 weeks prior to the in vivo study). Full recovery of body weight and food intake was achieved by day 7. Rats randomized for ribozyme treatment received an ICV injection of CPT1L-Ribo, CPT inhibitors or controls on day 17. The experimental group treated with TDGA received ICV injection of the inhibitor on day 21, 6 hr prior to the harvesting of brains. Panels B. and C. show quantitation of CPT1L (B) and CPT1M (C) mRNA by real-time PCR. RNA was purified from individual hypothalamic nuclei (PVN, LHA, and arcuate), which were obtained by micro punch technique 3 days after ICV injection of pTarget control (■; N=4) or CPT1LRibo (□; N=5). Copy number of CPT1 mRNA is normalized to β-Actin copy number ×10$^6$. Panels D. and E. show CPT1 activity in individual arcuate nuclei (D) or whole hypothalamus (E). Brains were harvested 6 hr or 3 days prior the ICV injection of TDGA or CPT1L-Ribo respectively, and arcuate nuclei were punched out. CPT1 activity was measured in the particulate fraction of protein extracts from animals treated with ICV control injections (■; N=6, receiving aCSF+2% DMSO or Control Ribo), TDGA (▫.; N=6), or CPTL-Ribo (□; N=5). Panels F and E establish that ICV administration of CPT1 inhibitors increases levels of LC-CoAs in arcuate. Levels of stearoyl-CoA (F) and oleyl-CoA (E) respectively were measured by HPLC in arcuate of rats injected ICV with control compound (■; ST1340) or ST1326 (□).

Based on these results, two specific inhibitors of CPT1 activity, ST1326 and 2-Tetradecylglydate (TDGA), or CPT1L-Ribo were infused ICV in conscious rats in order to decrease CPT1 activity and increase LC-CoAs in the hypothalamus. The baseline anthropometrical and biochemical characteristics of rats in each experimental group were similar compared with the appropriate control (Table 1). Of note, there was a tendency toward lower fasting plasma insulin and leptin levels in rats treated ICV with CPT1L-Ribo for three days compared with pair-fed controls (Table 1).

versely, CPT1L mRNA was expressed at much lower levels particularly in ARC and its expression was not appreciably altered by CPT1L-Ribo. If the marked decrease in CPT1L mRNA has important biological effects, it should also lead to a decrease in CPT1 activity in ARC. Thus, we next measured CPT1 activity in ARC and in whole hypothalamus. A marked decrease in CPT1 activity (FIG. 2d) was observed following ICV administration of CPT1L-Ribo in ARC but not in whole hypothalamus (FIG. 2e), in accord with the selective effects observed on CPT1L mRNA (FIG. 2b). We also validated the effect of the irreversible CPT1 inhibitor TDGA on CPT1 activity in ARC (FIG. 2d) and whole hypothalamus (FIG. 2e). Finally, we aimed to test the postulate that ICV administration of inhibitors of CPT1L activity would increase LC-CoAs in ARC. We used for this purpose the reversible CPT1L inhibitor ST1326 and its inactive stereo isomer ST1340 as a control. ICV ST1326 administration lead to a marked increase in stearoyl-CoA (FIG. 2f) and Oleyl-CoA (FIG. 2g) levels in ARC but not in PVN and LHA. Other LC-CoAs (not shown) were also significantly increased by ICV ST1326 administration. Thus, ICV delivery of molecular and pharmacological inhibitor of CPT1 effectively decreased CPT1 activity in ARC and the inhibition of CPT1L activity significantly raised the concentration of specific LC-CoAs. Based on these findings, two sets of experiments were designed to examine the effects of the hypothalamic inhibition of CPT1 activity on feeding behavior and insulin action.

Hypothalamic inhibition of CPT1 decreases food intake. First we examined whether central administration of molecu-

TABLE 1

|  | Vector | CPT1L-Ribo | Vehicle | TDGA | ST1340 | ST1326 |
|---|---|---|---|---|---|---|
| Basal: | | | | | | |
| Body wt. (g) | 286.9 ± 9 | 277 ± 8 | 345 ± 13 | 319 ± 10 | 307 ± 6 | 302 ± 4 |
| Food Intake (g) | 13 ± 3 | 14 ± 2 | 25 ± 2 | 25 ± 2 | 22 ± 3 | 21 ± 2 |
| Glucose (mM) | 8.1 ± 0.7 | 8.2 ± 0.6 | 8.1 ± 0.5 | 8.2 ± 0.8 | 8.0 ± 1.0 | 8.1 ± 0.7 |
| Insulin (ng/ml) | 1.2 ± 0.2 | 0.8 ± 0.2 | 2 ± 0.4 | 1.9 ± 0.1 | 1.4 ± 0.2 | 1.4 ± 0.2 |
| FFA (mM) | 0.6 ± 0.1 | 0.5 ± 0.1 | 0.6 ± 0.1 | 0.5 ± 0.1 | 0.4 ± 0.1 | 0.5 ± 0.1 |
| Leptin (ng/ml) | 1.0 ± 0.3 | 0.8 ± 0.1 | 1.5 ± 0.2 | 1.7 ± 0.1 | 0.9 ± 0.2 | 0.9 ± 0.1 |
| Clamp: | | | | | | |
| Glucose (mM) | 8.0 ± 0.8 | 8.1 ± 0.5 | 8.0 ± 0.8 | 8.1 ± 0.5 | 8.2 ± 0.9 | 8.1 ± 0.8 |
| Insulin (iU/ml) | 20 ± 2 | 21 ± 2 | 21 ± 2 | 25 ± 3 | 25 ± 4 | 21 ± 2 |
| FFA (mM) | 0.4 ± 0.1 | 0.4 ± 0.1 | 0.6 ± 0.1 | 0.5 ± 0.1 | 0.4 ± 0.1 | 0.4 ± 0.1 |

The values during the clamp represent steady-state levels obtained by averaging at least four plasma samples during the experimental period. In this experiment, the food intake in the vector group was matched to that of the CPT1L-Ribo group. Food intake in the remaining experimental groups was measured prior to the acute ICV infusion of test substances.

Figure 3:
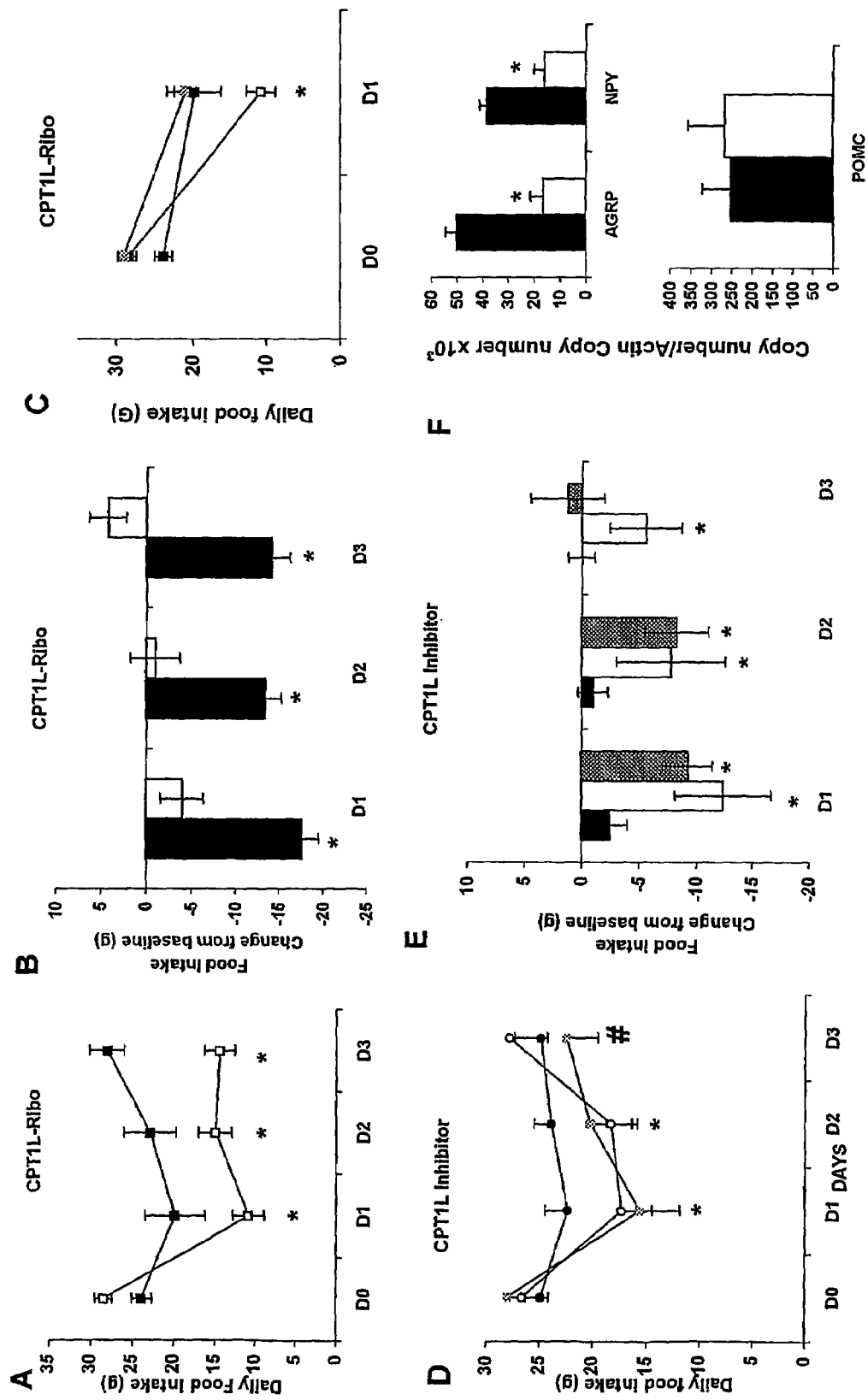
FIG. 3 shows graphs summarizing experimental data establishing that inhibition of hypothalamic CPT1L by genetic or pharmacological means decreases food intake. Panel A. Sprague-Dawley rats received on day 0 a single ICV injection of either CPT1L-Ribo plasmid (□) or control vector (■). Daily food intake was significantly suppressed from day 1 to day 3 following ICV injection of the CPT1L-Ribo. Panel B shows changes in food intake induced by ICV CPT1L-Ribo (□) vs. vector injection (■). Significant changes were detected compared with both baseline and vector. Panel C shows the effect on 24 hr food intake of ICV injection of CPT1L-Ribo (□) compared to ICV injection of vector control (■) or ribozyme control (▫.). Panel D shows daily food intake after a single ICV injection on day 0 of either ST1326 (5 pmoles, -⊕-, and 25 pmoles, -●-, respectively), or of the inactive stereo isomer ST1340 (25 pmoles, -○-). Both doses of ST 1326 caused an inhibition of food intake statistically significant on day 1 and 2. On day 3, only the high dose of ST1326 significantly lowered food intake compared to control group. Panel E shows changes in food intake induced by ICV ST1326 (5 pmoles, ▨ and 25 pmoles, □, respectively), or control ST1340 (■). Significant changes were detected with ICV ST1326 compared with baseline and ST1340. * P<0.001 vs. control group and baseline. # P<0.01 only for high dose ST1326 vs. control. Panel F shows down-regulation of CPT1L by ICV CPT1L-Ribo increases NPY and AgRP expression in ARC. Quantitative analysis by real-time PCR of NPY and AgRP (upper panel) and POMC (lower panel) in ARC of rats treated with vector control (■) or CPT1L-Ribo (□). Neuropeptides mRNA levels are expressed as copy number per β-actin copy number ×10$^3$.

ICV catheters were implanted in male Sprague-Dawley rats by stereotaxic surgery (Obici et al., 2002a; Obici et al., 2001; Liu et al., 1998). The biochemical or molecular analyses, the metabolic or the feeding experiments were performed ~3 weeks later following complete recovery from the operation (FIG. 2a). CPT1L-Ribo was delivered ICV three days prior to experimental tests (FIG. 2a). CPT1 inhibitors or vehicle (CON) were acutely injected or infused ICV for 6 hr in chronically catheterized Sprague Dawley rats (Obici et al., 2002a; Obici et al., 2001) (FIG. 2a). We first examined the effect CPT1L-Ribo on CPT1L (FIG. 2b) and CPT1M (FIG. 2c) mRNA levels in selected hypothalamic nuclei sampled by micro punches. Using quantitative real time PCR (adjusted for β-actin copy number) we demonstrated a marked decrease in CPT1L mRNA in the arcuate nuclei (ARC), but not in more lateral regions of the hypothalamus, such as the paraventricular nuclei (PVN) or the lateral hypothalamus (LHA). Conlar and pharmacological antagonists of CPT1 modulates feeding behavior in conscious rats (FIG. 3). To this end, three-hours before the onset of the dark cycle paired groups of rats received a bolus of either control vector or CPT1L-Ribo, or ST 1340, an inactive stereo isomer of ST 1326, or the CPT1 inhibitor (ST 1326) via an indwelling ICV catheter. Food intake was monitored in metabolic cages before and up to 72 h after the ICV injections (Obici et al., 2002a). The selective decrease in ARC CPT1L expression and activity (FIGS. 2b and d) via ICV injection of CPT1L-Ribo resulted in rapid onset of anorexia (FIG. 3a-c) starting on the first night following the ICV administration (average food intake 13.0±1.9 vs. 23.0±3.2 gr./day; p<0.01). The marked effect of ICV CPT1L-Ribo on food intake was significant when compared with either control vector or with an unrelated control ribozyme (FIG. 3c). Similarly, acute ICV injection of a potent and specific inhibitor of CPT1L (ST 1326) markedly inhibited food intake in rats while the inactive stereo isomer (ST 1340) failed to modify feeding behavior (FIG. 3d,e). The anorectic effect of central CPT1 inhibition lasted for at least 48 h following a single ICV administration. These decreases in food intake were significant compared with both baseline and vehicle/control (FIG. 3a-e). The changes from baseline induced by CPT1 inhibition were statistically significant at 24 h (−17.6±2.0 g and −12.4±3.9 g), and 48 h (−13.4±1.8 g and −7.8±3.8 g) following ICV administration of CP1L-Ribo and high dose ST 1326, respectively (FIGS. 3b and e). This represented a ~50% decrease in daily food intake, which returned toward baseline values by 72 h.

In order to begin investigating the mechanisms responsible for the anorectic properties of ARC CPT1 inhibition, we next analyzed the effect of CPT1L-Ribo on the gene expression of key ARC peptides. Quantitative analyses by real time PCR revealed a marked decrease in AgRP and NPY mRNA in the ARC of rats treated with ICV CPT1L-Ribo compared with Control-Ribo (FIG. 3f). Conversely, the expression of POMC in the ARC was not significantly altered by CPT1L-Ribo administration (FIG. 3f). Overall, these anorectic effects support the notion that changes in the neuronal levels of LC-CoAs may directly control food intake via their action on discrete hypothalamic centers. Furthermore, increases in LC-CoAs levels in selective hypothalamic neurons are likely to account for the potent effects of oleic acid and of FAS inhibitors on food intake (Loftus et al., 2000; Obici et al., 2002a; Makimura et al., 2001; Shimokawa et al., 2002).

Figure 4:
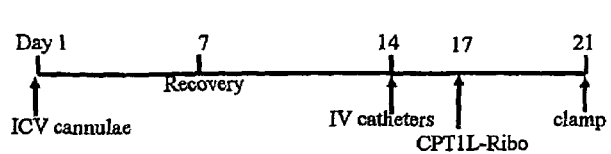
FIG. 4 shows graphs summarizing experimental results establishing that inhibition of hypothalamic CPT1 improves hepatic but not peripheral insulin action. Panel A shows a schematic representation of the experimental procedures. Surgical implantation of ICV cannulae was performed on day 1 (~3 weeks prior to the in vivo study). After complete recovery, IV catheters were placed on day 14 and ICV injections of CPT1L-Ribo or control vector was done on day 17. Finally, clamp studies were performed on day 21. Panel B shows a schematic representation of the pancreatic-insulin clamp procedure. The infusion studies lasted a total of 360 min. Rats received CPT1L-Ribo or vector control as a bolus injection three days prior to the clamp studies (as shown in FIG. 1I). All other groups received at t=0 a primed-continuous ICV infusion of either vehicle or CPT1 inhibitor, which was maintained for the remainder of the study. At t=120 an infusion of labeled glucose (HPLC-purified [$^3$H-3]-glucose; New England Nuclear, Boston, Mass.) was initiated and maintained for the last 4 hours of the study. Finally, pancreatic-insulin clamp study was initiated at t=120 min and lasted for 2 hours. This procedure involved the infusion of somatostatin (3 μg/kg/min), insulin (1 mU/kg/min), and glucose as needed to prevent hypoglycemia. The rate of insulin infusion was designed to replace normal basal levels in post absorptive rats. Panels B, D, and F show the rates of glucose disposal (Rd) prior (■) and during (□) pancreatic-insulin clamp studies in rats treated with ICV TDGA, ST1326 and CPT1L-Ribo compared to their appropriate controls. The Rd was not significantly affected by the ICV treatments. Panels C, E, and G show the rates of glucose production (GP) prior (■) and during (□) pancreatic-insulin clamp studies in rats treated with ICV TDGA, ST1326 and CPT1L-Ribo compared to their appropriate controls. GP was similar in all treatment groups before the start of the pancreatic-insulin clamp (■). During the pancreatic clamp, in the presence of ~basal insulin concentrations (□), ICV administration of TDGA, ST1326 and CPT1L-Ribo markedly inhibited GP compared with the respective ICV vehicle controls (p<0.01). Panel H shows that the inhibition of GP (% decrease from post absorptive level) in response to ~basal insulin concentrations was markedly enhanced by ICV administration of TDGA, ST1326 and CPT1L-Ribo as compared with their respective vehicles controls (aCSF+2% DMSO, ST1340, control vector).
Figure 4:
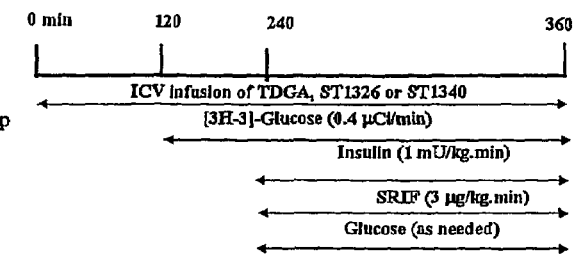
Figure 4:
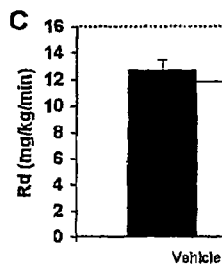
Figure 4:
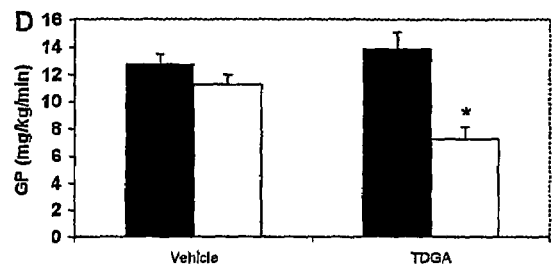
Figure 4:
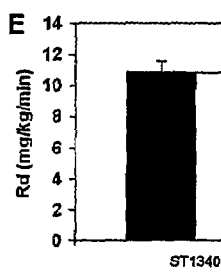
Figure 4:
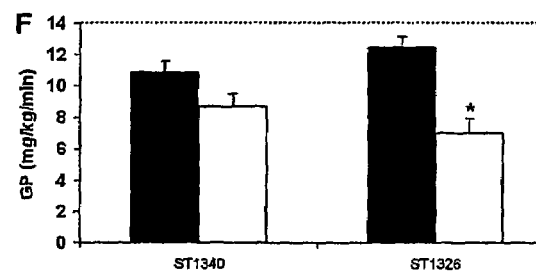
Figure 4:
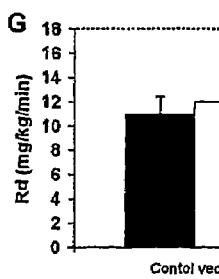
Figure 4:
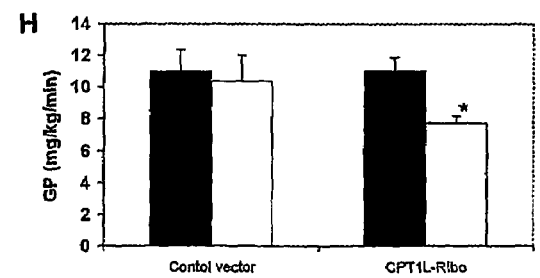
Figure 4:
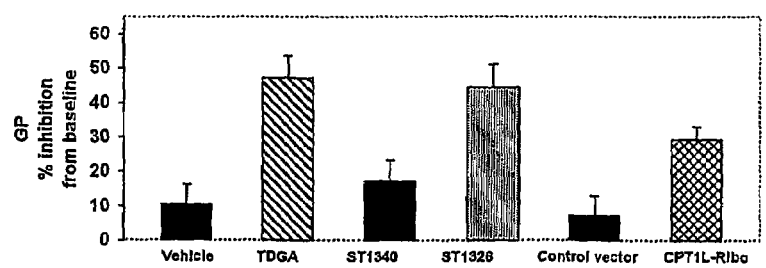

Hypothalamic inhibition of CPT1 inhibits glucose production. Experiments were also designed to examine the effect of central inhibition of CPT-1 on whole body insulin action (FIG. 4a,b). Insulin action was assessed by a combination of ICV infusions with systemic pancreatic-insulin clamp studies (FIG. 4b). In these studies, the daily food intake was matched in the rats receiving ICV vector and ICV CPT1L-Ribo (Table 1). All rats also received an intra-arterial infusion of [$3-^3H$]-glucose for the last 4 hr of ICV infusion and a pancreatic/insulin clamp (insulin 1 mU/kg.min; somatostatin 3 µg/kg/min) during the last 2 hr of the study (Obici et al., 2002a; Obici et al., 2001). As expected in the presence of ~basal circulating insulin levels (clamp procedure; Table 1), the rate of glucose infusion (GIR) required to maintain euglycemia was marginal in ICV control studies (vector-ST1340- or vehicle-infused animals; ~0.8 mg/kg/min). By contrast, following ICV infusion of inhibitors of CPT-1 expression or activity glucose had to be infused at the rate of ~5 mg/kg/min in order to prevent hypoglycemia. Thus, central inhibition of CPT-1 activity in the presence of fixed and basal insulin concentrations stimulates insulin action on glucose homeostasis.

We next examined the potential mechanism(s) by which ICV administration of CPT-1 antagonists enhances whole body insulin action. We assessed glucose kinetics by tracer dilution methodology (Obici et al., 2002a; Obici et al., 2001) in order to establish whether the increased GIR induced by central antagonists of CPT1 was due to stimulation of glucose uptake or to suppression of endogenous glucose production (GP). The rate of glucose uptake was not significantly affected by ICV treatments (FIG. 4c,e,g). Conversely, in the presence of basal and equal insulin levels (~20 µU/ml), GP was markedly and significantly decreased (FIG. 4d,f,h) by ICV CPT1L-Ribo (by 30±3%; n=5), ST1326 (by 44±7%; n=8), and TDGA (by 47±6%; n=7). These decreases in glucose output completely accounted for the effect of central inhibition of CPT1 on whole body glucose metabolism.

Discussion

On the basis of these results, we conclude that the central inhibition of CPT1 activity is sufficient to markedly suppress food intake and endogenous glucose production. Furthermore, we propose that the central inhibition of CPT1 activity leads to increased levels of LC-CoA in selective hypothalamic neurons. This increase represents a central signal of 'nutrient abundance', which in turn activates a chain of neuronal events designed to promote a switch in fuel sources from carbohydrates to lipids and to limit the further entry of exogenous and endogenous nutrients in the circulation.

Taken together with the potent effects of the central delivery of the long-chain fatty acid oleic acid and of FAS inhibitors (Loftus et al., 2000; Obici et al., 2002a; Makimura et al., 2001; Shimokawa et al., 2002), the present findings support the notion that an increase in the cellular levels of LC-CoAs in hypothalamic neurons is an important sensor of increased nutrient availability (FIG. 1a). This in turn activates central neuronal pathways involved in the regulation of both energy homeostasis and hepatic insulin action. Since glucose production by the liver is the major source of endogenous fuel, central neural circuitries concomitantly modulate exogenous and endogenous sources of energy (Obici et al., 2002a; Obici et al., 2001). This is consistent with a negative feedback system designed to monitor and regulate the input of nutrients in the circulation in response to changes in their availability.

Since circulating free fatty acids can gain rapid access to the central nervous system (Miller et al., 1987; Goto & Spitzer, 1971), changes in hypothalamic fatty acid oxidation are likely to modulate the regulation of energy balance and insulin action via changes in neuronal LC-CoA levels. Under physiological conditions, inhibition of hypothalamic CPT1 activity is likely to occur when neuronal levels of malonyl-CoA are elevated. An increase in cellular malonyl-CoA levels is generally induced by increased metabolism of carbohydrates. Thus, this hypothetical 'central lipid signal' would be generated when availability of LCFA is coupled with increased availability of carbohydrates (increased malonyl-CoA). Since inhibition of hypothalamic CPT1 activity per se reproduced the effects of ICV administration of the LCFA oleic acid (Obici et al., 2002a) on food intake and on glucose production, it is likely that the accumulation of LC-CoAs rather than their flux into the mitochondria is a key component of hypothalamic lipid sensing. This is also consistent with the observation that marked increase in the availability of the short chain fatty acid octanoic acid (Id.) failed to reproduce the potent effects of oleic acid on glucose production (Id.). It should be noted that while malonyl-CoA is likely to play an important role in the physiological regulation of hypothalamic CPT1 activity, it is unlikely that an increase in malonyl-CoA levels occurred herein in the presence of genetic or pharmacological inhibition of CPT1 activity. In fact, inhibition of CPT1 activity results in increased levels of LC-CoAs, which in turn decrease malonyl-CoA levels via inhibition of ACC (Lunzer et al., 1977).

Finally, the potent orexigenic (appetite-stimulating) effects of cannabinoids and the potent anorectic effects of CB, receptor (Blazquez et al., 1999) antagonism may also be partly mediated via modulation of hypothalamic CPT-1 activity and of LC-CoA levels. In fact, endocannabinoids stimulate CPT1 activity and fatty acid oxidation in cultured astrocytes independently of malonyl-CoA and via interaction with CB1 receptors (Di Marzo et al., 2001). Central inhibition of fatty acid oxidation may thus represent an innovative approach to the prevention and treatment of obesity and type 2 diabetes mellitus.

Methods

Design and cloning of CPT1L Ribozyme. Two complementary 51-base long oligonucleotides (ODN), 5'-CTGTAC-CAAAGAGCTGATGAGTCCGTGAGGAC-GAAACGCCGCTCACAATGA-3' (SEQ ID NO:2), and 5'-CATTGTGAGCGGCGTTTCGTCCTCACG-GACTCATCAGCTCTTTGGTACAGA-3' (SEQ ID NO:3) were synthesized (Operon Technologies, Inc., Alameda, Calif.), which contained a catalytic core of a hammerhead ribozyme sequence (shown above in bold characters, see also FIG. 1c), flanked by a 13-nucleotide long sequence from the liver isoform of carnitine palmitoyltransferase 1 (CPT1L) (Esser et al., 1993; Birikh et al., 1997). The double stranded fragment resulting from the annealing of the two ODNs was inserted into a mammalian expression vector (pTargeT from Stratagene). The CPT1L-Ribo cassette contains a cytomegalovirus (CMV) enhancer/promoter, an intron element upstream of the CPT1L-Ribo, and a downstream simian virus 40 late polyadenylation site. (FIG. 1d). The resulting CPT1L-Ribo construct would direct the transcription of a hammerhead catalytic RNA specific for CPT1L mRNA (FIG. 1e). Control studies were done with either pTarget vector alone, when indicated, or a ribozyme control plasmid (RiboC) in which the CPT-specific sequences were replaced by the random sequence 5'-GGAGCCTCGAGATCTGATGAGTC-CGTGAGGACGAAACTGTGAGCGTTTGG-3' (SEQ ID NO:4).

Expression of CPT1L Ribozyme. CPT1L-Ribo plasmid or vector alone were transfected into AtT20 cells with polyethilenimine (PEI-Sigma-Aldrich, MW 25,000) as previously described (Boussif et al., 1995). Northern analysis was performed on a pool of ~200 independent clones. For in vivo expression, CPT1L-Ribo plasmid was complexed to PEI and injected ICV as previously described (Goula et al., 1998). Briefly, 5 µl of D5W (5% glucose solution) containing 5 µg of plasmid was mixed with 5 µl of 18 mM PEI in D5W. vAfter 10 min incubation at room temperature, the 10 µl mixture was infused ICV at a rate of 1 µl/min.

Brain stereotaxic micro punches. Brain micro punches of individual hypothalamic nuclei were prepared as previously described (Palkovits, 1973; Obici et al., 2002b).

Quantitation of CPT1 and neuropeptides mRNA by Northern and real-time PCR. CPT1 probes specific for liver and muscle isoforms (CPT1L and M, respectively) were amplified by polymerase-chain reaction (PCR) using rat hypothalamus RNA as template and cloned into pTarget. CPT1lL probe spanned 755 nucleotides from position 10 to 765 of CPT1L cDNA (GeneBank accession number L07736); CPT1M probe spanned 545 nucleotides from position 688 to 1233 of CPT1M cDNA (GeneBank accession number NM_013200).

Total RNA was isolated with Trizol (Invitrogen, Carlsbad, Calif.) from individual hypothalamic nuclei (i.e. Arcuate, PVN etc.). Single strand cDNA synthesis and real-time PCR reactions were performed as previously described (Obici et al., 2002b). CPT1L and CPT1M mRNA specific primers contained the following sequences: CPT1L forward (F) 5'-CTCCGAGCTCAGTGAGGACCTAAAG-3' (SEQ ID NO:5) and reverse (R) primer, 5'-CAAATACCACTG-CAATTTGTG-3' (SEQ ID NO:6); CPT1M F 5'-CCAGACT-GCAGAAATACCTGGTGCTC-3' (SEQ ID NO:7) and R 5'-GTTCTGACGTGCTTCTGCCCACTCTAC-3' (SEQ ID NO:8). Hypothalamic neuropeptides expression was performed by real-time PCR using the following primers: NPY-F 5'-GCCATGATGCTAGGTAACAAACG-3' (SEQ ID NO:9), R 5'-GTTTCATTTCCCATCACCACATG-3' (SEQ ID NO:10), POMC-F 5'-CCAGGCAACGGAGATGAAC-3' (SEQ ID NO:11), R 5'-TCACTGGCCCTTCTTGTGC-3' (SEQ ID NO:12), AgRP-F 5'-GCCATGCTGACTGCAAT-GTT-3' (SEQ ID NO:13), R 5'-TGGCTAGGTGCGACTA-CAGA-3' (SEQ ID NO:14), and β-actin F 5'-TGAGACCT-TCAACACCCCAGCC-3' (SEQ ID NO:15), R 5'-GAGTACTTGCGCTCAGGAGGAG-3' (SEQ ID NO:16). Transcript levels are expressed as copy number of each gene normalized to copy number for β-actin. Copy number for each transcript was measured against a standard curve, which was obtained by PCR runs of each primer set with serial dilutions of a plasmid containing the target template sequences.

Animal preparation for in vivo experiments. We studied ninety-three 10-week old male Sprague-Dawley rats (Charles River Breeding Laboratories, Wilmington, Mass.). Rats were housed in individual cages and subjected to a standard light-dark cycle. Three weeks prior to the in vivo studies, we placed a chronic catheter in the third cerebral ventricle by stereotaxic surgery (Obici et al., 2002a; Obici et al., 2001; Liu et al., 1998). One week before the pancreatic-insulin clamp protocols, we placed additional catheters in the right internal jugular and left carotid artery (Obici et al., 2001; Liu et al., 1998). All ICV solutions were dissolved in artificial cerebral spinal fluid (aCSF). Food intake was monitored daily.

Effect of central inhibition of CPT1 and food intake. We examined the effects of ICV CPT1L-Ribo and ST 1326 on food intake. Three-hours before the start of the dark cycle, CPT1L-Ribo or vector control, ST 1326 or ST 1340 was injected as a bolus via indwelling catheters implanted in the third cerebral ventricle. In the feeding studies, rats received a single bolus injection of 25 pmoles of ST1340 or two different doses (5 and 25 pmoles) of ST1326. Rats were adapted to the metabolic cages and their daily food intake had been constant (changes <10%) for a minimum of three consecutive days preceding the ICV injections. Food intake was continuously monitored for the following 72 h.

Measurements of in vivo glucose kinetics and pancreatic-insulin clamp procedure. The infusion studies lasted a total of 360 min (FIG. 3a). Briefly, at t=0 min a primed-continuous ICV infusion of either CPT1 inhibitors or control solution was initiated and maintained for the remainder of the study. 2-tetradecylglydate (TDGA, a gift from Dr. Manuel Guzman) was dissolved in DMSO, diluted into aCSF (Harvard Apparatus) and infused ICV at a rate of 50 pmoles/hr. ST1326 [(R)-N-(tetradecylcarbamoyl)-aminocarnitine] and ST1340 (the inactive stereo isomer of ST1326) [(S)-N-(tetradecylcarbamoyl)-aminocarnitine] were dissolved in aCSF and infused at a rate of 50 pmoles/hr. Prior to the pancreatic-insulin clamp studies, rats receiving ICV injection of either CPT1L-Ribo or vector control three days prior to the clamp procedure were randomized into two pair-fed experimental groups. A primed-continuous infusion of HPLC-purified [3-$^3$H]-glucose (New England Nuclear, Boston, Mass.; 40 µCi bolus, 0.4 µCi/min) was started at t=120 min and continued for the duration of the study (Obici et al., 2002a; Obici et al., 2001; Liu et al., 1998). Finally, a pancreatic-insulin clamp (Obici et al., 2002a; Obici et al., 2001; Liu et al., 1998) was initiated at t=240 min and lasted for 2 hours. This procedure involved the infusion of somatostatin (3 µg/kg/min), insulin (1 mU/kg/min), and glucose as needed to prevent hypoglycemia, or antibodies against C peptide (Linco) and Melanocortin Receptor type 2 (Chemicon). The rate of insulin infusion was designed to replace normal basal levels in postabsorptive rats.

Steady state conditions for plasma glucose and insulin concentration and glucose specific activity were achieved in all experiments during the last 60 minutes of the clamp procedure. Radioactivity of [$^3$H]glucose in plasma was measured from supernatants of Ba(OH)$_2$ and ZnSO$_4$ precipitates after evaporation to dryness for the removal of tritiated water (Somogyi pellet). The specific activity of tritiated water in plasma (Somogyi filtrate) was determined from the total counts of the protein-free supernatant before and after evaporation to dryness. Under steady state conditions for plasma glucose concentration, the rate of glucose disappearance (Rd) equals the rate of glucose appearance (Ra). Ra was determined from the ratio of the infusion rate for [$^3$H]glucose (disintegrations per minute) and the specific activity of plasma [$^3$H]glucose (disintegrations per minute per mmol glucose) under steady state conditions. The rate of glucose production (GP) was equal to Ra under basal conditions and it was obtained from the difference between Ra and the rate of glucose infusion during the pancreatic clamp period.

All values are presented as the mean±SE. Comparisons among groups were made using analysis of variance or unpaired students t test as appropriate. The study protocol was reviewed and approved by the Institutional Animal Care and Use Committee of the Albert Einstein College of Medicine.

Example 2

Modulation of Long-Chain Co-A Levels (LC-CoAs) in the Hypothalamus Regulates Food Intake and Glucose Production This example describes experiments using methods described in Example 1.

Diet-induced obesity results in a marked decrease in hypothalamic LC-CoAs. In order to test whether a decrease in hypothalamic 'lipid signal' could play a role in diet-induced obesity, we measured the levels of LC-CoAs in the Arcuate nuclei (ARC) of rats fed a highly palatable diet for three days (Obici et al., 2002a). The latter is an excellent model for human obesity and diet-induced insulin resistance since it is not based on a single gene defect. Despite receiving a diet very rich in saturated fatty acids, the levels of ARC LC-CoAs were decreased by ~60% in over-fed rats compared with either rats on a regular chow or with rats on the high fat regimen pair-fad with the regular chow rats. These surprising results support the presence of a deficient negative feed-back between circulating nutrients and hypothalamic energy centers in animals predisposed to weight gain.

Inhibition of hypothalamic CPT-1 markedly improves hepatic insulin action in rats with diet-induced obesity and insulin resistance. Here, we hypothesized that inhibition of hypothalamic CPT-1 could decrease glucose production (GP) in over-fed rats. Thus, we examined whether decreasing hypothalamic oxidation of LC acutely suppresses GP in rats on a highly palatable high fat diet (33% of calories from fat). To inhibit the entry of LC in the mitochondria, we infused ICV a selective inhibitor of CPT-1 activity (CPT1) or its inactive stereoisomer (CON) in conscious rats. CPT1 or CON was acutely infused ICV for 6 hr in chronically catheterized rats. In the presence of basal insulin levels, glucose infusion was required to prevent hypoglycemia in the CPT1 (4.2±0.4 mg/kg/min), but not in the CON (0.5±0.2 mg/kg/min) group. GP was markedly and significantly decreased by CPT1 (−37±5%; p<0.01; n=4) but not by ICV CON (+3±7%; n=5). We postulate that the lack of metabolic response to the central administration of LC in over-fed rats is due to increased activity of neuronal CPT-1.

Central inhibition of CPT1 activity should be an effective treatment for diet-induced insulin resistance. Overall, the data presented above validate the notion that any pharmacological mean of increasing the ARC concentrations of LC-CoAs is a valid and novel approach to the prevention and treatment of obesity and type 2 diabetes mellitus. In addition to selective inhibitors of CPT-1 activity or expression, other enzymes can be targeted in order to decrease LC-CoA metabolism. For example, the inhibition of ARC LC-CoA hydrolases or tioesterases will also increase LC-CoAs and is expected to decrease GP and food intake. Similarly, increasing the levels of hypothalamic malonyl-CoA via inhibition of malonyl-CoA decarboxylase or via stimulation of acetyl-CoA carboxylase is also likely to inhibit food intake and glucose output. Finally, increased neuronal activity of fatty acid transporter proteins or LC-CoA synthetase should also increase hypothalamic levels of LC-CoAs and therefore inhibit glucose production and food intake.

In conclusion, this Example establishes that increasing the hypothalamic levels of LC-CoAs decreases food intake and glucose production.

Example 3

Hypothalamic Responses to Long-chain Fatty Acids are Nutritionally Regulated

Example Summary

Central administration of the long-chain fatty acid oleic acid inhibits food intake and glucose production in rats. Here we examine whether short-term changes in nutrient availability can modulate these metabolic and behavioral effects of oleic acid. Rats were divided into three groups receiving a highly palatable energy-dense diet at increasing daily caloric levels (below, similar, or above the average of rats fed standard chow). Following three days on the assigned diet regimen, rats were tested for acute biological responses to the infusion of oleic acid in the third cerebral ventricle. Three days of overfeeding virtually obliterated the metabolic and anorectic effects of the central administration of oleic acid. Furthermore, the infusion of oleic acid in the third cerebral ventricle failed to decrease the expression of neuropeptide Y in the hypothalamus and of glucose-6-phosphatase in the liver following short-term overfeeding. The lack of hypothalamic responses to oleic acid following short term overfeeding is likely to contribute to the rapid onset of weight gain and hepatic insulin resistance in this animal model.

Introduction

Obesity and type 2 diabetes mellitus (DM2) share several metabolic features, which include insulin resistance (Kahn and Flier, 2000; Kopelman and Hitman, 1998; Porte et al., 1998). The incidence of obesity and DM2 has risen significantly in developed and developing countries. For example, in the US alone there has been a significant increase in the prevalence of obesity among both children and adults over the last ten years (Flegal et al., 2002; Ogden et al., 2002). Consumption of high calorie diets and sedentary lifestyles play major roles in this trend (Kopelman and Hitmanl Flegal et al., 2002; Friedman, 2000). Similarly, exposure to palatable diets with high caloric density (high in fat) induces a variable degree of weight gain and insulin resistance in mice (West et al., 1992; West et al., 1995), rats (Kraegen et al., 1991; Schemmel et al., 1970; Sclafani and Springer, 1976), pigs (Romsos et al., 1978), dogs (Hall et al., 1995), and monkeys (Ausman et al., 1981).

Evolutionary pressures may have favored the selection of genes, which maximize energy storage when food availability is high (Coleman, 1978; Coleman, 1979; Neel, 1999; Wang et al., 2001). Others and we have proposed that a rapid increase in caloric intake initiates a "tug of war" between peripheral 'anabolic signals' (Kersten, 2001) and hypothalamic 'catabolic signals' (Woods et al., 1998; Loftus et al., 2000; Obici et al., 2002a; 2002d; 2002e; 2002f; 2003). The effects of hormones, such as leptin (Zhang et al., 1994; Schwartz et al., 1996a; 1996b; Frederich et al., 1995; Cinti et al., 1997) and insulin (Obici et al., 2002e; 2002f; Woods et al., 1979; Brief and Davis, 1984), and nutrients, such as fatty acids (Loftus et al., 2002; Obici et al., 2002a; Obici et al., 2003), within the hypothalamus initiate a negative feedback, which includes restraint on food intake, stimulation of energy expenditure, and decreased output of nutrients from endogenous sources (mainly from the liver). Animals and humans may be susceptible to weight gain and altered metabolic regulation when this negative feedback is disrupted. The rapid onset of leptin resistance in rodent models of voluntary overfeeding provides initial support for this theory (Halaas et al., 1997; Widdowson et al., 1997).

Here we test the hypothesis that short-term increase in caloric intake rapidly induces resistance to the central effects of the long chain fatty acid, oleic acid (OA). Thus, we examined whether changes in nutritional status lead to alterations in the central effects of OA on feeding behavior and glucose production.

Abbreviations

ICV, in the third cerebral ventricle; OA, oleic acid; NPY, neuropeptide Y; DM2, type 2 diabetes mellitus; PEPCK, phosphoenolpyruvate carboxykinase; Glc-6-Pase, glucose-6-phosphatase; HPB, hydroxypropyl-β-ciclodextrin, SC, standard chow, HF, high fat chow; LCFA, long chain fatty acid Experimental Procedures Animals and Experimental Design. Ten week-old male Sprague-Dawley (S-D) rats (Charles River Breeding Laboratories, Inc., Wilmington, Mass.) were housed in individual cages and subjected to a standard light dark cycle (0600-1800/1800-0600). At 14 days before the in vivo studies, all rats received implantations of ICV catheters by stereotaxic surgery as previously described (36). Rats were allowed to recover completely before initiation of all in vivo studies. Animals were fed a standard chow (SC, cat. no. 5001, Purina Mills Ltd, with 59% calories provided by carbohydrate, 28% by protein and 12% by fat, 3.3 kcal/g), a high sucrose (HS; animals were given free access to a 20% sucrose solution in addition to their standard chow diet), or a highly palatable high fat diet (HF, cat. no. 9389; Purina Mills Ltd., with 45% calories provided by carbohydrate, 22% by protein and 33% by fat, 5.32 kcal/g) which was designed by the supplementation of the SC diet with 10% lard. The lard contained 2% myristic acid, 24% palmitic acid, 13% stearic acid, 46% oleic acid, and 12% linoleic acid. The total composition of fats in the HF diet was 5.2% saturated, 6.2% monounsaturated, and 2.7% polyunsaturated fat by weight. The SC diet contained 1%, 1.5%, and 1.6% of saturated, monounsaturated, and polyunsaturated fats by weight, respectively. Five groups of animals ere included in the feeding and metabolic studies (described below) after three days on the following diet regimens (Table 2): 1) SC ad libitum (SC; ~80 kcal/day); 2) HS ad libitum (HS; ~95 kcal/day); 3) HF ad libitum (HF140; ~140 kcal/day); 4) HF calorie restricted (HF55; ~55 kcal/day); and 5) HF pair-fed to SC(HF80; ~80 kcal/day).

Central Delivery of OA. OA was complexed with the polymer hydroxypropyl-3-cyclodextrin (HPB, CTD Inc). The latter has been shown to provide an excellent vehicle for the central delivery of fatty acids (Obici et al., 2002a; Yaksh et al., 1991; Pitha et al., 1994). OA was solubilized in 45% HPB to a final concentration of 17 mM. The HPB-OA solution was diluted in artificial cerebral spinal fluid (aCSF) to the appropriate concentration used for each ICV injections (30 or 300 nmol/5 μl). HPB alone at a similar concentration as in the OA studies was used in all vehicle control studies.

Figure 5:
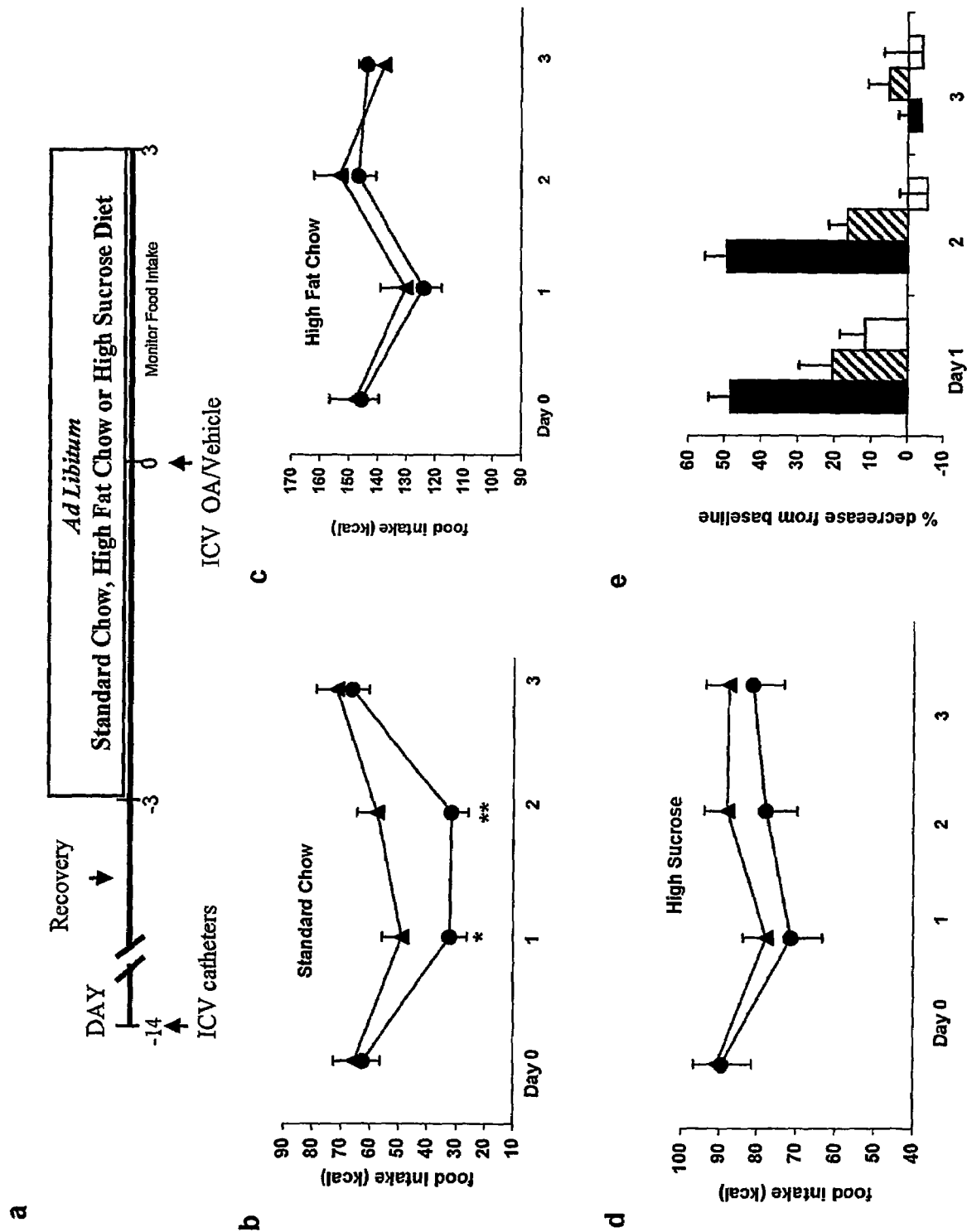
FIG. 5 is a schematic representation of a protocol and graphs of experimental results showing the effect of ICV oleic acid (OA) on daily food intake in animals fed standard, high fat chow, or high sucrose. Panel a shows a schematic representation of the experimental design for the feeding experiments. Following recovery from ICV implantation surgery, all rats were allowed to eat ad libitum their standard chow. Three days before the ICV injections (day-3), a group of animals was switched to a highly palatable diet (high fat or high sucrose) while another group was kept on standard chow. All groups were allowed to eat ad libitun and their daily food intake was recorded to provide baseline values. On day 0, OA (30 nmol) or vehicle (HPB) were injected as an ICV bolus. Daily food intake was monitored for three days post-injection in all groups. Panel b shows that, in animals fed standard chow, ICV OA (●) resulted in rapid onset of anorexia, which lasted for 48 h. ICV vehicle (▲) did not significantly modify eating behavior. Panel c shows that, in animals fed high fat chow, neither ICV OA (●) nor ICV vehicle (▲) significantly affected daily food intake. Panel d shows that, in animals fed a high sucrose diet, ICV OA (●) did not significantly change food intake compared to ICV vehicle (▲). Panel e shows changes in daily food intake, expressed as percent decrease from baseline (average of day -2, -1, and 0), one, two, and three days following injection of ICV OA in animals fed standard (■), high sucrose (▫), or high-fat (□) chow. ICV Office Action markedly decreased food intake (by ~50%) for 2 days in rats receiving standard chow; however, ICV OA failed to significantly alter feeding behavior in rats receiving high sucrose or high fat chow. Values are mean±SEM. *P<0.001 vs. vehicle, **P<0.0001 vs. vehicle, #P<0.05 vs. standard chow group.

Feeding Behavior Studies. This experimental protocol was designed to examine the acute effect of ICV OA on food intake in three experimental groups fed a standard chow (SC), a high sucrose diet (HS95) and a high fat diet (HF140). SC and HF140 animals were allowed to eat their diets ad libitum. HS animals were given free access to a 20% sucrose solution in addition to the standard chow diet for three days. Following three days of ad libitum feeding in all groups, on study day 0 (FIG. 5a), rats were given an ICV bolus injection of either 5 ml of OA (30 nmol) or vehicle at a rate of 1 μl/min using a gas-tight syringe (Hamilton Corp) one hour before the start of the dark cycle. Food intake was measured at the same time daily for three days post-injection.

NPY Expression Studies. For analysis of NPY expression, we studied two groups of rats, HF55 and HF140. After three days on the respective diet regimen, ICV Vehicle (10% HPB in aCSF) or ICV OA (30 nmol) was injected as a bolus into the third cerebral ventricle one hour before the start of the dark cycle. Food was withdrawn and hypothalami were harvested 16 hrs following injection.

Insulin action studies. The experimental protocol herein was designed to examine the effect of nutritional status on the ability of long-chain fatty acids in the hypothalamus to modulate carbohydrate metabolism. Rats (n=43) were implanted with chronic catheters as previously described (Liu et al., 1998). After full recovery from the catheterization, animals were randomized into three groups HF55 (n=16), HF80 (n=9), or HF140 (n=18) and were allowed to consume their allocated diet for three days. On the night prior to the in vivo study all rats received 55 kcal to ensure a similar nutritional state at the start of the metabolic studies. All studies were performed in awake, unstressed, chronically catheterized rats. At t=−120 (FIG. 7a), a primed-continuous infusion of ICV OA (total dose 30- or 300-nmol) or Vehicle (HBP 10% in aCSF) was initiated and maintained throughout the duration of the study. Plasma glucose was measured periodically initiating at the onset (t=−120) of the ICV infusion and lasting throughout the duration of the study. Plasma samples for determination of insulin, leptin, and non-esterified fatty acid concentration were obtained at the onset (t=−120) and at 30 min intervals during the study. At t=0, and a primed-continuous infusion of HPLC-purified [3-3H]-glucose (New England Nuclear, Boston, Mass.; 40 μCi bolus, 0.4 μCi/min for duration of the study) was initiated and maintained for the last four hours of the study. Samples for determination of $^3$H-glucose specific activity were obtained at 10-minute intervals throughout infusions. Finally, at t=120, a pancreatic-insulin clamp study was initiated and maintained for two hours. During this procedure, a primed-continuous infusion of regular insulin (1 mU/kg/min) was administered, and a variable infusion of 25% glucose solution was started at t=120 and periodically adjusted to clamp the plasma glucose concentration at ~7 mM. The rate of insulin infusion was designed to replace the plasma insulin concentration at ~the average basal levels in post-absorptive rats. In order to control for possible effects of the ICV injections on endocrine pancreas, somatostatin (3 μg/kg/min) was coinfused with insulin to inhibit endogenous insulin secretion. At the end of the in vivo studies, rats were anesthetized (pentobarbital 55 mg/kg body weight, intravenously) and tissue samples were freeze-clamped in situ with aluminum tongs pre-cooled in liquid nitrogen. All tissue samples were stored at −80° C. for subsequent analysis.

Analytical Procedures and Calculations. Plasma glucose was measured by the glucose oxidase method (Glucose Analyzer II, Beckman Instruments, Inc. Fullerton, Calif., USA). Plasma insulin and leptin levels were determined by RIA (rat Leptin RIA kit, Linco Research Inc., St. Charles, Mo.). Serum adiponectin was measured by RIA (Linco Research, Inc., St. Charles, Mo.). Plasma non-esterified fatty acid concentrations were determined an enzymatic method by an automated kit according to the manufacturer's specifications (Waco Pure Chemical Industries. Osaka, Japan). The radioactivity of [3-$^3$H]glucose in plasma was measured from supernatants of Ba(OH)$_2$ and from ZnSO$_4$ precipitates (Somogyi procedure), after each was evaporated to dryness for the removal of tritiated water. Hepatic uridine diphosphoglucose (UDP-glucose) concentrations and specific activities were obtained by two sequential chromatographic separations, as previously described (Giaccari and Rossetti, 1989; 1992; Rossetti et al., 1993; 1996). Calculations were performed as described (Barzilai et al., 1997).

Northern Blot Analysis. Total RNA was isolated from hypothalami and liver with Trizol (Invitrogen Corp., California, USA). NPY, Glc-6-Pase or PEPCK expression was measured by northern blot analysis. Hypothalamic RNA was analyzed using probes for prepro-NPY and β-actin. To assess the effect of ICV OA on the expression of hepatic enzymes, total RNA was isolated from freeze-clamped liver tissues from rats subjected to insulin clamp studies. Glc-6-Pase and PEPCK cDNA were obtained as previously described (Combs et al., 2001; Massillon et al., 1996; 1998). Probes were labeled with [α-$^{32}$P] dCTP using a random primer kit (Stratagene). Quantification was performed by scanning densitometry, normalizing for β-actin signal and 18S ribosomal RNA to correct for loading variabilities.

Comparisons between groups were made by analysis of variance and all values are presented as the mean±S.E. Specifically, for the feeding data presented in FIG. 5 the two curves for vehicle and oleic acid were first compared to each other using analysis of variance for repeated measures. If statistical differences (between curves) were revealed, the differences between each time point were estimated using student t test.

The study protocol was reviewed and approved by the Institutional Animal Care and Use Committee of the Albert Einstein College of Medicine.

Results

To induce voluntary hyperphagia, male S-D rats were fed a highly palatable diet, ad libitum, for three days (Table 2). Their food intake and adaptation to the increased caloric content of the diet was monitored daily. Despite hyperleptinemia and hyperinsulinemia, animals in this group failed to adapt to the enhanced caloric content of the diet and increased their daily energy intake by ~70% to ~140 kcal/day. Since littermates undergoing the same experimental procedures consumed ~80 kcal/day when exposed to standard chow, we also compared the ad libitum fed rats to a group of pair-fed rats receiving 80-kcal per day and to a group of caloric restricted rats receiving 55-kcal/day of the same highly palatable diet. This approach allowed us to investigate the central effects of OA at three levels of daily caloric intake reflecting moderate caloric restriction, pairfeeding, and over-feeding. It should be noted that data reported below for the pair-fed group are quite similar to those obtained in rats fed standard chow (Obici et al., 2002a). Thus, this experimental approach allowed us to examine whether the central effects of oleic acid (OA) on food intake and insulin action are modulated by short-term changes in caloric intake.

TABLE 2

General Characteristics of the Experimental Groups. Data are means ± SE. The values during clamp represent steady-state levels obtained by averaging at least five plasma samples during the experimental period.

| | Treatment | | | | | | |
|---|---|---|---|---|---|---|---|
| | HF55 Vehicle | HF55 OA | HF80 Vehicle | HF80 OA | HF140 Vehicle | HF140 OA (30 nmol) | HF140 OA (300 nmol) |
| N: | 9 | 7 | 4 | 5 | 7 | 6 | 5 |
| Basal: | | | | | | | |
| Food Intake(kcal/d) | 55 | 55 | 80 | 80 | 143 ± 6 | 137 ± 6 | 150 ± 4 |
| Body Weight (g) | 293 ± 10 | 295 ± 6 | 303 ± 3 | −307 ± 4 | 313 ± 10 | 312 ± 12 | 301 ± 9 |
| Δ Body Weight (g) | −8 ± 6 | −15 ± 3 | −2 ± 11 | −3 ± 8 | 17 ± 6* | 13 ± 4* | 11 ± 3* |
| Glucose (mmol/l) | 7.4 ± 0.2 | 7.4 ± 0.2 | 7.8 ± 0.1 | 7.2 ± 0.3 | 7.6 ± 0.2 | 7.4 ± 0.1 | 7.4 ± 0.2 |
| Insulin (ng/ml) | 0.8 ± 0.2 | 0.7 ± 0.3 | 0.8 ± 0.3 | 0.8 ± 0.2 | 1.7 ± 0.2* | 1.7 ± 0.4* | 1.8 ± 0.4* |
| Leptin (ng/ml) | 1.2 ± 0.2 | 1.3 ± 0.2 | 1.0 ± 0.1 | 1.0 ± 0.1 | 2.1 ± 0.4* | 1.8 ± 0.2* | 2.0 ± 0.3* |
| FFA (mmol/l) | 0.4 ± 0.1 | 0.5 ± 0.1 | 0.5 ± 0.1 | 0.4 ± 0.1 | 0.4 ± 0.1 | 0.4 ± 0.1 | 0.5 ± 0.1 |
| Adiponectin(μg/ml) | 4.0 ± 0.8 | 3.6 ± 0.5 | 3.0 ± 0.3 | 2.9 ± 0.4 | 3.5 ± 0.2 | 3.8 ± 0.3 | 4.0 ± 0.5 |
| Clamp: | | | | | | | |
| Glucose (mmol/l) | 7.5 ± 0.2 | 7.3 ± 0.3 | 7.8 ± 0.1 | 7.1 ± 0.3 | 7.0 ± 0.4 | 7.5 ± 0.2 | 7.8 ± 0.3 |
| Insulin (ng/ml) | 0.8 ± 0.2 | 0.8 ± 0.2 | 0.9 ± 0.2 | 0.8 ± 0.1 | 1.1 ± 0.1 | 1.1 ± 0.2 | 1.2 ± 0.1 |
| Leptin (ng/ml) | 1.0 ± 0.2 | 0.9 ± 0.1 | 1.1 ± 0.2 | 1.0 ± 0.1 | 2.0 ± 0.4* | 1.6 ± 0.2* | 1.9 ± 0.4* |
| FFA (mmol/l) | 0.4 ± 0.1 | 0.4 ± 0.1 | 0.5 ± 0.1 | 0.4 ± 0.1 | 0.4 ± 0.1 | 0.4 ± 0.1 | 0.5 ± 0.1 |

*P < 0.01 vs. HF55 or HF80.

Voluntary overfeeding rapidly curtails the effects of central OA on feeding behavior and hypothalamic NPY expression. We examined whether ICV OA modulates feeding behavior in animals following three days of voluntary overfeeding. Food intake was monitored daily in animals fed ad libitum either a high palatable diet (HF140) to induce hyperphagia or a standard chow (SC; caloric intake 78±3 kcal/day) diet for three days prior to ICV injections. In order to examine the effects of macronutrient composition of the diet (e.g. high fat vs. high carbohydrate) on OA sensitivity, we also studied an additional group of animals that were allowed free access to a 20% sucrose solution in addition to their standard chow (HS; caloric intake of 93±4 kcal/day, reflecting an increased total caloric intake of ~20% compared to SC animals). After three days on their assigned regimen, all animals received a bolus of either OA (30 nmol) or Vehicle (HPB) via an indwelling ICV catheter one hour prior to the onset of the dark cycle. Food intake was monitored for a total of 3 days following ICV injections (FIG. 5a) and the effects of OA were compared to those elicited by vehicle alone within each experimental group. ICV OA resulted in a 48% and 52% decrease in food intake compared with pre-injection basal levels when administered to SC animals (FIG. 5b,e) on the first and second day following the ICV injection, respectively. However, after three days of moderate over-feeding (HS95) ICV OA decreased daily food intake by 21% on the first day and by 17% on the second day (FIG. 5d,e). Finally, following three days of marked voluntary hyperphagia (HF140), ICV OA decreased daily food intake by only 11% on the first day and by −2% on the second day (FIG. 5c,e). The modest decreases observed in the HS95 and HF140 groups were not statistically different from those observed after ICV injection of vehicle alone (FIG. 5c,d). All groups returned to baseline food intake 3 days after the OA injection (FIG. 5b-e).

Figure 6:
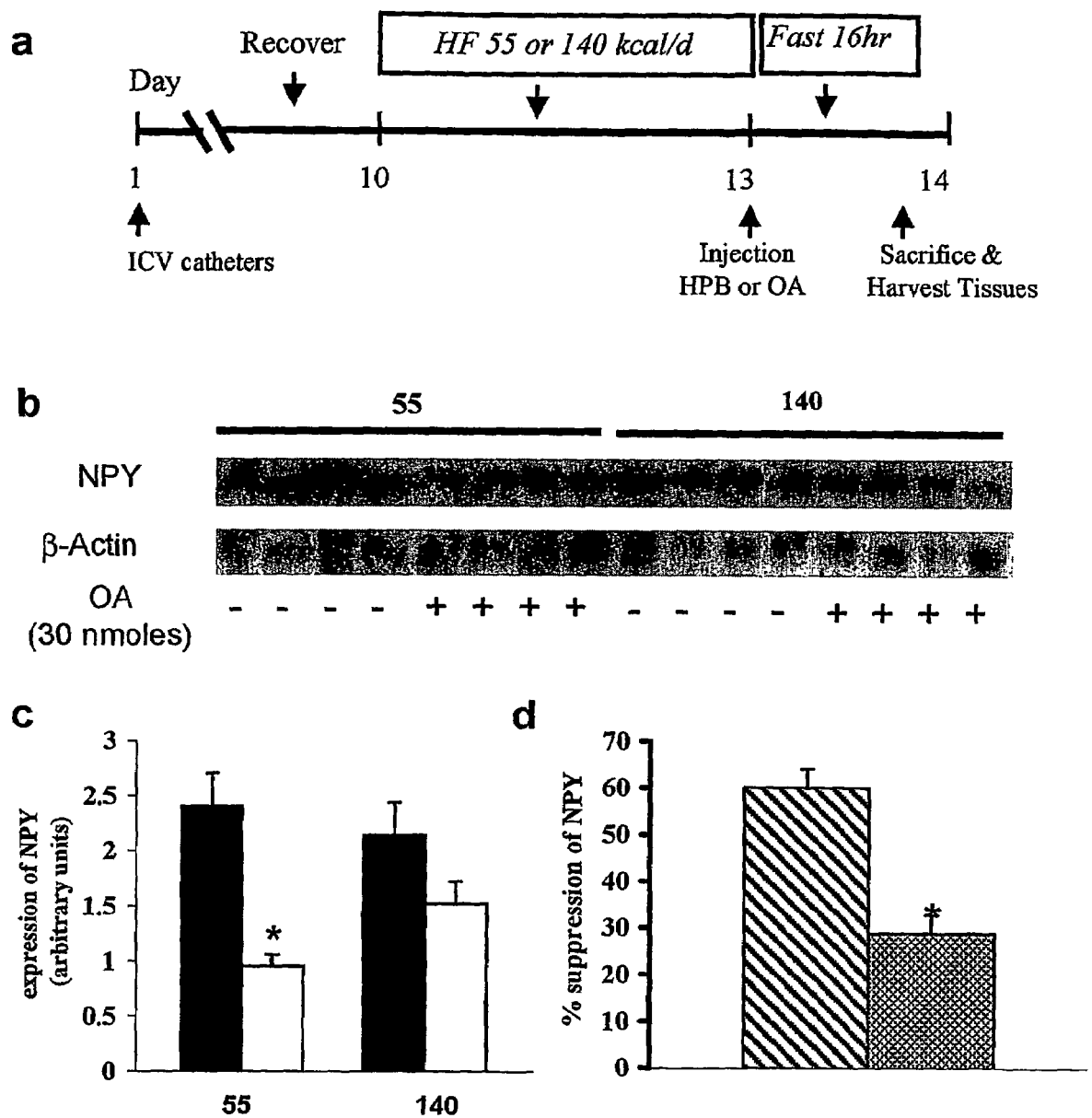
FIG. 6 is a schematic representation of a protocol, and photographs and graphs of experimental results showing that the effect of ICV OA on hypothalamic NPY expression is nutritionally modulated. Panel a is a schematic representation of experimental design for hypothalamic NPY expression determinations. Ten days after surgical implantation of ICV catheters and following full recovery of all experimental animals, rats were fed high fat chow at either 55 kcal/d (55) or ad libitun (140) for three days. On day thirteen, OA (+ in Panel b; n=6/group) or vehicle (−; n=6/group) were then injected as an ICV bolus 1 hr before the start of the dark cycle. Following ICV injections, food was withdrawn and hypothalami were harvested 16 hrs following injection. Panel b shows photographs of representative blots from northern analysis of hypothalamic NPY mRNA. This analysis demonstrated a decrease in hypothalamic NPY mRNA after ICV OA in rats fed 55 kcal/d compared with ICV vehicle. However, ICV OA did not significantly alter NPY mRNA in rats fed ad libitum. Panel c shows quantification of the northern blot analysis by densitometry, which documented that ICV oleic acid (□) significantly decreased hypothalamic NPY expression compared with ICV vehicle (■) in animals fed 55 kcal/d. ICV OA failed to significantly modify hypothalamic NPY expression in animals fed ad libitum. Panel d shows data expressed as percent decrease in hypothalamic NPY mRNA induced by ICV OA compared with ICV vehicle in animals fed 55 kcal/d (left bar) or ad libitum (right bar). All data are normalized for β-actin. #$P<0.05$ vs. 55 kcal/d.

We next examined a potential mechanism by which resistance to hypothalamic OA may develop. We previously reported that hypothalamic NPY mRNA was decreased (by ~50%) after ICV OA compared with ICV vehicle in rats fed standard chow following prolonged (16 h) fasting (Obici et al., 2002a). Here we asked whether changes in the nutritional status modulate ICV OA's ability to restrain the hypothalamic expression of NPY. To this end, we assessed the abundance of NPY mRNA in the hypothalamus by northern blot analysis following three days of ad libitum feeding (~140 kcal/d) on a highly palatable diet or 55 kcal/d on the same diet. Both experimental groups were given a single bolus injection of 30 nmol OA or vehicle (HPB) followed by an overnight fast. Hypothalamic tissue was harvested the following morning and northern blot analysis was performed (FIG. 6a). Quantification by densitometry, utilizing β-actin as a reference transcript, demonstrated that the average NPY mRNA levels were similar in HF55 and HF140 (FIG. 6c). ICV OA suppressed NPY mRNA expression in the 55-kcal/d group by ~60% (FIG. 6d). This decrease is similar to that previously reported in rats fed standard chow at ~70 kcal/d following prolonged fasting (Obici et al., 2002a). However, ICV OA decreased hypothalamic NPY mRNA by only 28% in fasted animals following three days of voluntary overfeeding (FIG. 6c,d). These data provide evidence that the hyperphagia displayed in animals given free access to a highly palatable diet is partly due to defective regulation of NPY expression in the hypothalamus.

Figure 7:
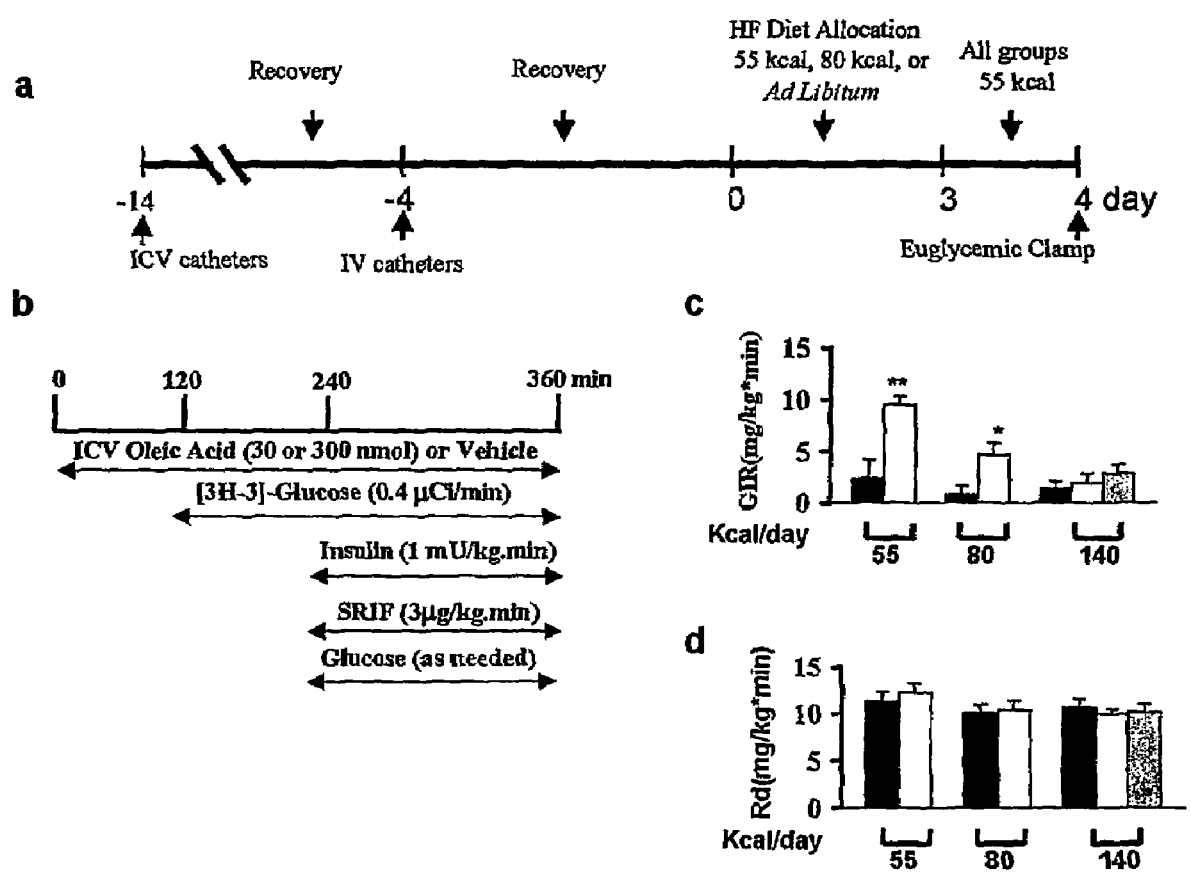
FIG. 7 shows schematics of protocols and graphs of experimental results showing that the effect of ICV OA on whole body insulin action is modulated by daily caloric intake. Panel a is a schematic representation of the experimental design for the pancreatic-insulin clamp studies. Surgical implantation of ICV catheters was performed at least two weeks before diet interventions in order to allow time for adequate recovery. Similarly the implantation of intravascular catheters was completed 4 days before diet interventions. On day 0, rats were administered high fat chow at 55 kcal/d, 80 kcal/d, or ad libitum (~140 kcal/d) for three days. On the evening preceding the clamp procedures, all rats received a fixed portion of food (55 kcal) to ensure that they were in a comparable post-absorptive state at the start of the metabolic experiments. Panel b shows a schematic of the pancreatic-insulin clamp procedure. ICV OA or vehicle infusions were initiated at the beginning of the study (t=−120) and lasted throughout the duration of the entire clamp procedure. Infusion of labeled glucose began at t=0 and was continued for the last 4 h of the study. Finally, the infusions of somatostatin and insulin were initiated at t=120 and lasted for the remaining 2 hours. A 25% glucose solution was infused as needed to prevent any decline in the plasma glucose concentration. Panel c shows the glucose infusion rate (GIR) during pancreatic-insulin clamp studies. In the presence of ICV injection of HPB (■) and ~basal insulin concentrations, GIR was negligible in all groups. However, during ICV injection of OA (□), exogenous glucose at the rate of ~4.5 and 9 mg/kg/min was required to prevent hypoglycemia in the groups receiving 55 and 80 kcal/d, respectively. In the group fed ad libitum (140), GIR was less than 2 mg/kg/min in the presence of ICV vehicle, low dose (30 nmol, □) and high dose (300 nmol, ▨) OA infusion. Panel d shows that the rate of glucose disappearance (Rd) during the pancreatic-insulin clamp period. The Rd was not significantly affected by ICV OA in any of the experimental groups. **$P=0.0001$ vs. vehicle infusion, *$P<0.03$ vs. vehicle infusion.

Voluntary overfeeding rapidly blunts the effects of central OA on insulin action and hepatic glucose production. We next examined whether short-term changes in nutritional status were sufficient to alter the effect of OA on in vivo insulin action (FIG. 7a). The effect of ICV OA on insulin action was assessed in conscious rats using a combination of ICV infusions and pancreatic-insulin clamp studies (FIG. 7b). The three experimental groups (HF55, HF80, and HF140) were randomized to receive either ICV OA or vehicle (HPB) treatment (Table 2 and FIG. 7b). The basal plasma FFA and glucose concentrations were similar in all groups (Table 2). On the day prior to pancreatic-euglycemic clamp studies, all rats received the same amount of calories (55 kcal) to ensure similar post-absorptive state prior to metabolic measurements (FIG. 7a). In the presence of ICV vehicle and near basal levels of circulating insulin, marginal rates of glucose infusion (GIR) were required to maintain euglycemia in the three experimental groups (HF55-2.4, HF80-1.2, and HF140-1.4 mg/kg/min) (FIG. 3c). In contrast, in both the HF55 and HF80 groups, following the ICV infusion of OA (30 nmol) the GIR required to maintain euglycemia was markedly increased (9.55 and 4.64 mg/kg/min, respectively). However, ICV infusion of the same dose of OA failed to increase GIR in the ad libitum fed group. In fact, even the infusion of a 10-fold higher dose of OA (300 nmol) did not significantly increase GIR in this group (FIG. 7c). Since the stimulatory effect of ICV OA on GIR was significantly (~2-fold) higher in the HF55 than in the HF80 group, this increase appears to be highly dependent on the preceding nutritional status of the animal even within the normal to low range of caloric intake. Plasma FFA concentrations did not change during the clamp period (Table 2) indicating that the metabolic effects induced by ICV OA were initiated by its action within the central nervous system (CNS).

Figure 8:
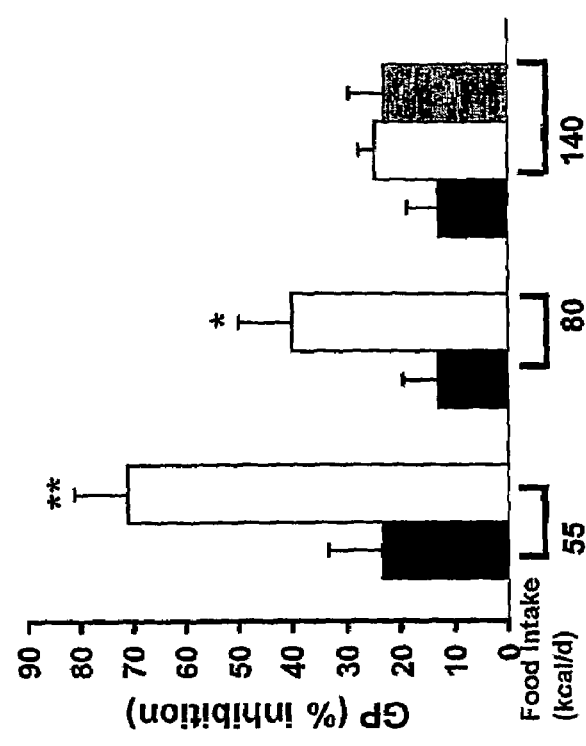
FIG. 8 is graphs of experimental results showing that the effect of ICV OA on hepatic insulin action is modulated by daily caloric intake and is a function of weight gain and daily caloric intake. Panel a shows the rate of glucose production (GP). In the presence of ~basal insulin concentrations, ICV administration of OA (□) markedly inhibited the rate of GP in the 55 and 80 kcal/d groups as compared with the correspondent vehicles (■). By contrast, ICV OA at low (30 nmol, □) and high (300 nmol, ▨) doses failed to significantly alter GP in over-fed rats (140) as compared with vehicle and high OA. Panel b shows the changes in GP during ICV OA and vehicle treatment. Changes in GP are expressed as % inhibition from baseline. Rats receiving either 55- or 80 kcal/d displayed a dramatic decrease in GP following ICV OA infusion (□) during the pancreatic clamp procedure as compared with the correspondent vehicles (■). However, in the ad libitum fed group (140), the change in GP induced by ICV OA at 30 nmol (□) or 300 nmol (▨) was similar to that induced by vehicle. **$P<0.001$ vs. vehicle infusion, *$P=0.05$ vs. vehicle infusion. Panels c and d shows the percent changes in endogenous glucose production (GP) induced by ICV vehicle and OA are plotted against percent decreases in body weight and daily food intake during the three days preceding the ICV injections. Panel c shows that, in the presence of ICV OA, the percent inhibition in GP was directly correlated with percent decreases in body weight. Panel d shows that, in the presence of ICV OA, the percent inhibition in GP was directly correlated with percent decreases in daily caloric intake.
Figure 8:
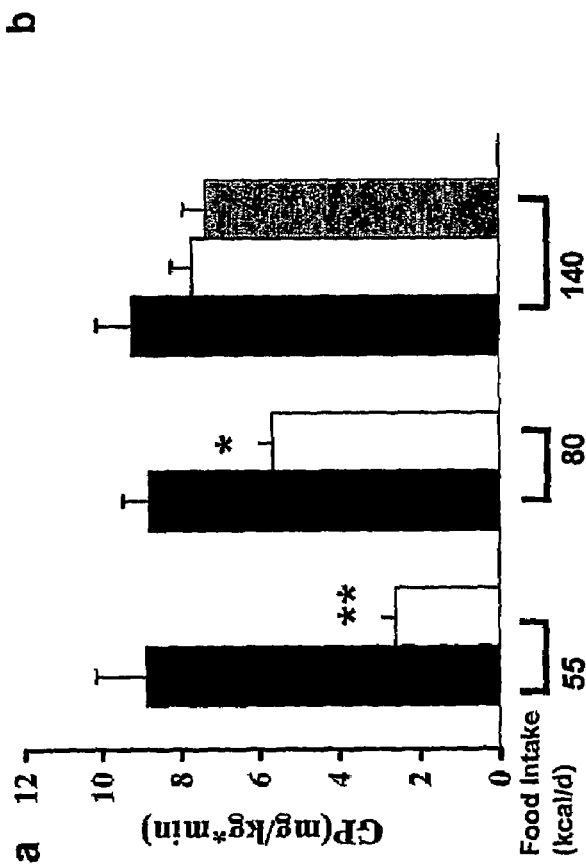
Figure 8:
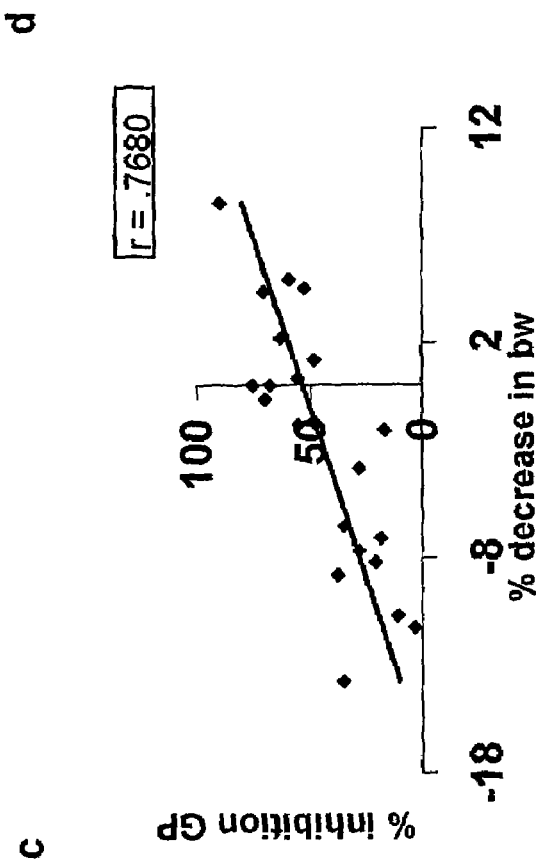

The increased requirement for exogenous glucose elicited by the ICV administration of OA in the presence of basal insulin levels could be due to stimulation of glucose uptake and/or to suppression of endogenous glucose production (GP). However, the rates of glucose disappearance (Rd in FIG. 7d) were similar in the three experimental groups and most importantly ICV OA did not significantly modify them. Thus, the increase in whole body insulin action induced by ICV OA in the HF55 and HF80 groups did not reflect an increase in peripheral glucose uptake (FIG. 7d). On the other hand, ICV OA (at 30 nmol) markedly inhibited GP in the HF55 and HF80 groups, but not in the ad libitum fed rats (HF140). Indeed, a 10-fold higher central infusion of OA also failed to significantly decrease GP in the ad libitum fed group (FIG. 8a). Consistent with the effect observed on GIR, the inhibition of GP by ICV OA was more pronounced (71% decrease from basal) in the HF55 group than in the HF80 group (−45% decrease from basal) (FIG. 8b). Finally, the inhibition of GP induced by ICV OA entirely accounted for its stimulation of GIR. To further examine the impact of the nutritional status in modulating the effect of ICV OA on metabolic fluxes we plotted the changes in GP induced by ICV OA or vehicle as a function of percent decreases in body weight (FIG. 8c) and daily food intake (FIG. 8d). The inhibitory effect of ICV OA was directly proportional to the decrease in daily food intake and weight gain. Importantly, there was no significant correlation between changes in GP and GIR and changes in food intake/body weight in the groups receiving ICV vehicle (data not shown). A similar correlation with OA induced inhibition of GP was also found by plotting only rats fed ad libitum the standard chow at various levels of caloric intake (data not shown). Thus, the degree of inhibition of GP in response to central administration of OA appears to be highly dependent on short-term changes in caloric intake and/or body weight.

Figure 9:
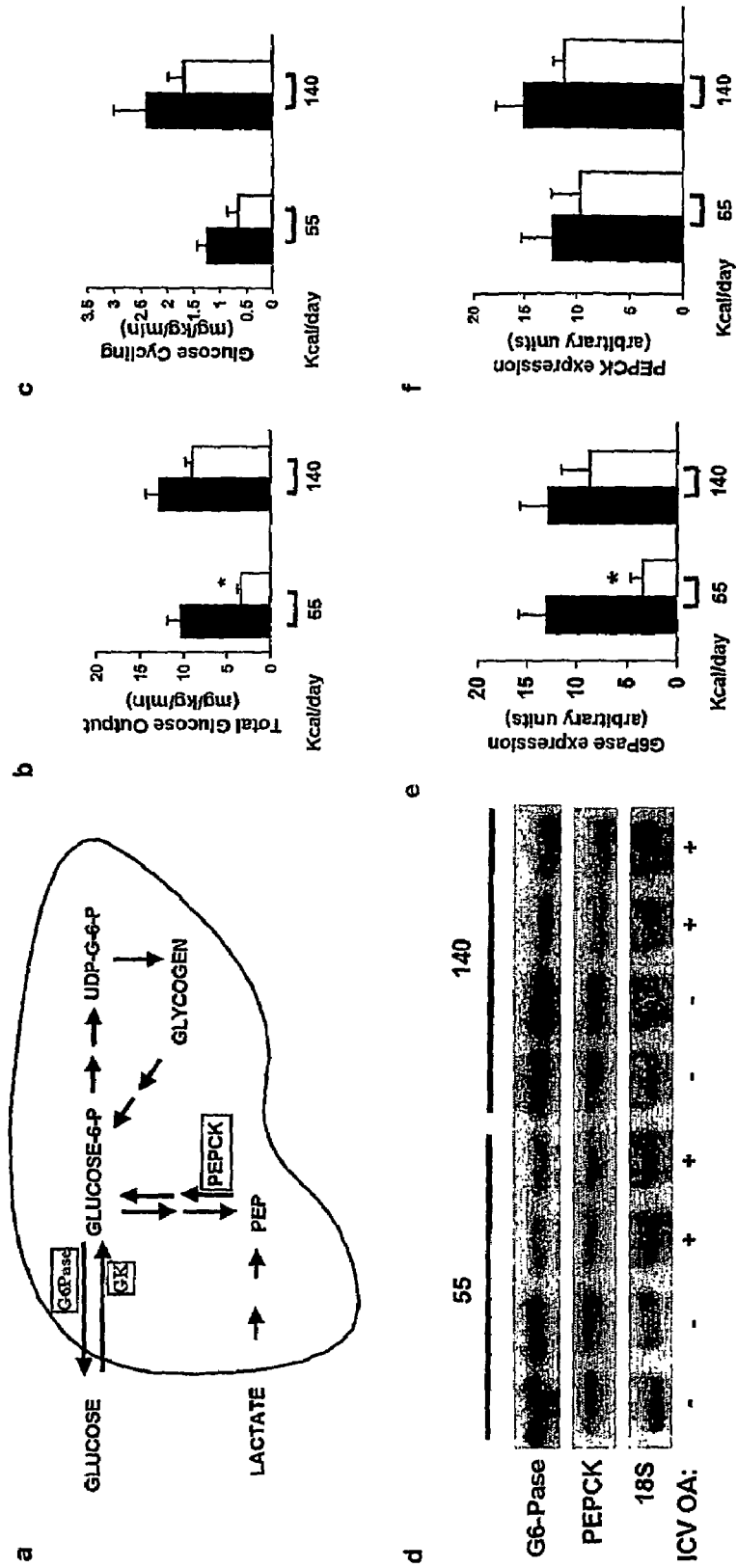
FIG. 9 is a schematic, photographs and graphs showing the effect of ICV OA on hepatic glucose fluxes and Glucose-6-Pase/PEPCK gene expression. Panel a is a schematic representation of hepatic glucose fluxes. GP represents the net contribution of glucosyl units derived from gluconeogenesis (largely via phosphoenolpyruvate, PEP) and from the breakdown of glycogen to the hepatic glucose-6-phosphate (glucose-6-P) pool. However, a portion of glucose entering the liver via phosphorylation by glucokinase (GK) is also a substrate for de-phosphorylation via glucose-6-Pase (G6 Pase). This futile cycle between glucokinase and glucose-6-Pase is commonly named glucose cycling and accounts for the difference between the total glucose output (flux through glucose-6-Pase) and GP. Panel b shows the effect of ICV OA (□) as compared to vehicle (■) on total glucose output (in vivo flux through glucose-6-phosphatase) in rats receiving 55 or 140 kcal/d. ICV OA markedly suppressed total glucose output in caloric restricted but not in over-fed rats. Panel c shows the effect of ICV OA on total glucose cycling in rats receiving 55 or 140 kcal/d. ICV OA (□) modestly and similarly decreased glucose cycling in caloric restricted and in over-fed rats as compared to vehicle (■). Panel d shows photographs of blots of northern analysis of the gluconeogenic enzymes Glucose-6-Pase and PEPCK in animals fed 55 or 140 kcal/d for three days prior to ICV OA (+) or vehicle (−) infusions. Panel e shows the quantification of northern blots for G6 Pase by densitometry. ICV OA (□) significantly decreased hepatic G6 Pase expression (by 73%) compared with ICV vehicle (■) in 55 kcal/d animals but not in animals consuming 140 kcal/d. Panel f shows the quantification of northern blots for PEPCK by densitometry. ICV OA (□) did not significantly decrease PEPCK expression in 55 or 140 kcal/d as compared with ICV vehicle (■). *$P<0.05$ vs. vehicle.

ICV OA markedly decreases the in vivo flux through Glc-6-Pase. GP represents the net contribution of glucosyl units derived from gluconeogenesis and glycogenolysis. However, a portion of glucose entering the liver via phophorylation by glucokinase is also a substrate for de-phosphorylation via Glc-6-Pase. This futile cycle between glucokinase and Glc-6-Pase is commonly named glucose cycling and accounts for the difference between the total glucose output (flux through Glc-6-Pase) and GP (FIG. 9a).

In order to further delineate the mechanisms responsible for the effect of ICV OA infusion on hepatic glucose production we estimated the in vivo flux through Glc-6-Pase and the relative contribution of glucose cycling to glucose output (Table 3; FIG. 9b,c). FIG. 9b,c depict the effect of ICV OA and ICV vehicle on the rates of hepatic glucose fluxes during the pancreatic-insulin clamp procedure. In the presence of similar plasma insulin concentrations, the rate of glucose production (as shown in FIG. 8a) was decreased by ICV Office Action in the HF55 and HF80 but not in the ad libitum fed rats (HF140). Table 3 displays the [$^3$H]-UDP-glucose, and the [$^3$H]-glucose specific activities used to calculate the contribution of plasma glucose (% Direct in Table 3) to the hepatic glucose-6-phosphate pool. These data allowed us to estimate the in vivo fluxes through Glc-6-Pase (total glucose output in FIG. 9b) and the rates of glucose cycling (FIG. 9c) in all groups. As shown in FIG. 9b, ICV OA markedly decreased the flux through Glc-6-Pase in parallel with the effect on GP in HF55 animals. Consistent with this marked decrease in overall glucose output the rate of glucose cycling was also decreased in rats receiving ICV OA compared with ICV vehicle (FIG. 9c). However, the decline in the rate of glucose cycling was much less pronounced than the decline in Glc-6-Pase flux and indeed it did not achieve statistical significance. The latter finding taken together with the moderate increase in the % direct pathway (Table 3) is consistent with a stimulatory effect of central OA on hepatic glucose phosphorylation. Thus, short-term central infusion of OA leads to marked decrease in the net de-phosphorylation of glucose-6-phosphate to glucose, which is largely due to diminished in vivo flux through Glc-6-Pase coupled with a moderate stimulation of the in vivo flux through glucokinase. These effects of ICV OA are blunted after three days of voluntary overfeeding.

TABLE 3

Effect of ICV OA on the "direct" pathway of hepatic UDP glucose formation. Specific activities of plasma glucose and hepatic UDPglucose (UDPGlc) were used to calculate the contribution of plasma glucose to the hepatic UDPglucose pool following [$^3$H-3]-glucose infusions in rats at the completion of pancreatic/insulin clamp studies.

| Kcal/d | HF55 | | HF140 | |
|---|---|---|---|---|
| ICV | Vehicle | OA | Vehicle | OA |
| UDPglucose Liver SA (dpm/nmol) | 6.8 ± 1.0 | 7.4 ± 2.0 | 9.7 ± 1.1 | 10.0 ± 1.4 |
| $^3$H-Glucose Plasma SA (dpm/nmol) | 55.8 ± 5.4 | 41.2 ± 4.2 | 58.2 ± 3.7 | 54.5 ± 3.1 |
| % Direct | 12 ± 3 | 17 ± 4 | 17 ± 3 | 18 ± 2 |

Effect of ICV OA on the hepatic expression of Glc-6-Pase and PEPCK. The potent effects of the central administration of OA on hepatic glucose fluxes prompted us to examine whether changes in the liver mRNA levels of key metabolic enzymes can partly account for these effects. Thus, we next measured the liver abundance of Glc-6-Pase and PEPCK mRNA as a function of 18S ribosomal RNA (FIG. 9d) or β-actin mRNA (not shown) in tissue samples obtained after ICV infusion of either OA or vehicle in caloric restricted and over-fed rats. ICV OA markedly decreased glucose-6-phosphatase gene expression in caloric restricted rats. Quantification of multiple blots by densitometry (FIG. 9e,f), utilizing β-actin as a reference transcript, demonstrated that ICV OA suppressed Glc-6-Pase mRNA expression in the HF55 group by ~73% with no changes detected in the HF140 group. Conversely, ICV OA failed to significantly alter the liver expression of PEPCK in either group. The marked inhibitory effect of ICV OA on liver Glc-6-pase expression is likely to contribute to its potent inhibition of the in vivo flux through glucose-6-phosphatase in caloric restricted rats.

Discussion

The development of obesity and DM2 is influenced by a complex interaction of environmental and genetic factors (Friedman, 2003; Hill and Peters, 1998; Ravussin and Gautier, 1999). Others and we have advanced the notion that common central pathways are able to elicit a response to nutrient availability that includes changes in both feeding behavior and metabolic processes (Woods et al., 1998; Obici et al., 2002e; 2002f; Barzilai et al., 1997; Shimomura et al., 1999; Spiegelman and Flier, 2001; Wang et al., 1997; Schwartz et al., 2000. In this regard, nutrient-dependent signals (e.g., leptin and insulin) convey the nutritional status of an organism to the hypothalamus, where messages are integrated and transduced into efferent signals that are aimed to limit the input of exogenous and endogenous nutrients into the circulation. Furthermore, it has been recently postulated that lipid metabolism within selective hypothalamic neurons is a primary biochemical sensor for nutrient availability, which in turn exerts a negative feed back on food intake (Loftus et al., 2000; Obici et al., 2002a; 2003) and endogenous glucose production (Obici et al., 2002a; 2003) (GP). In fact, central administration of fatty acid synthase (FAS) inhibitors (Loftus et al., 2000), of carnitine-palmitoyl-transferase-1 (CPT-1) antagonists (Obici et al., 2003), or of the LCFA oleic acid (Obici et al., 2002a), leads to decreased food intake (Obici et al., 2002d; 2002e; Zhang et al., 1994) and inhibition of endogenous glucose production (Obici et al., 2002e; Zhang et al., 1994). Based on these findings, we have postulated that a common effect of these central anorectic agents is to increase the cellular concentration of LCFA-CoAs within the arcuate nuclei of the hypothalamus (Obici et al., 2003). The latter increase may in turn take part in a negative feedback system that is intended to regulate the amount of nutrients in the circulation in response to changes in their availability (Obici et al., 2003).

Here we report that the ability of a central administration of the long-chain fatty acid oleic acid to inhibit food intake and hypothalamic NPY expression is blunted following three days of voluntary over-feeding in rats. Similarly, exposure to a highly palatable diet leading to hyperphagia induces resistance to the anorectic and metabolic effects of leptin and insulin in the hypothalamus in susceptible animal models (Friedman, 2000; Coleman, 1979; Neel, 1999; Wang et al., 2001). Neuropeptide Y (NPY), a potent orexogenic neuropeptide, is a downstream target of both leptin and insulin in the hypothalamus and their failure to restrain NPY may partially explain why common forms of obesity are characterized by normal or elevated food intake despite elevated plasma leptin and insulin levels. Of interest, NPY is also a downstream target of LCFA-CoAs as central administration of either oleic acid, FAS or CPT1 inhibitors prevents the rise in hypothalamic NPY mRNA induced by fasting (Loftus et al., 2000; Obici et al., 2002a; 2003). The impaired suppression of hypothalamic NPY expression by fatty acids observed in over-fed rats may play a particularly important role in determining the degree of hyperphagia following a period of fasting when circulating fatty acids are elevated and plasma leptin and insulin levels are low. However, it should also be kept in mind that the cellular metabolism of fatty acids within the hypothalamus is also likely to play a key role in modulating this nutrient signal (Zhang et al., 1994). In this regard, the well-established biochemical link between cellular carbohydrate and lipid metabolism may play a particularly important role. In fact, we hypothesize that the cellular levels of LCFA-CoAs are likely to represent the key signal generated in response to increased availability of fatty acids. Similarly, an increase in the availability of simple carbohydrates (such as sucrose) can markedly increase the cellular levels of LCFA-CoAs via increased levels of (glycolytically-derived) malonyl-CoA leading to inhibition of fatty acid oxidation. Thus, it is likely that this central nutrient-sensing mechanism may be able to respond to increased availability of either lipids or carbohydrate. It is in turn possible that the sustained increase in cellular LCFA-CoAs leads to adaptive changes in cellular lipid metabolism (e.g., inhibition of ACC leading to decreased formation of malonyl-CoA). In keeping with this postulate, we found that increasing the daily caloric intake via either a high fat or a high sucrose diet similarly blunted the effect of ICV OA on food intake, suggesting that changes in daily caloric intake rather than in macronutrient composition of the diet are likely to account for this effect. In this regard, it is intriguing that the anorectic effects of the FAS inhibitor C75 are preserved in diet-induced and genetic obesity in mice (Thupari et al., 2002). By contrast, the poor response to ICV OA in overfed rats may be secondary to decreased esterification of LCFA due to decreased activity of acyl-CoA synthase or increased activity of acyl-thioesterases and/or accelerated metabolism of LCFA-CoAs due to increased activity of CPT1 or depletion of malonyl-CoA. As in other models of diet-induced obesity (Friedman, 2000; Coleman, 1979; Neel, 1999; Wang et al., 2001), the lack of response to an anorectic agent may indicate impaired action (of oleic acid) on feeding behavior and/or inability to counteract the high palatability of the high fat and high sucrose diets.

Why does a short-term increase in food intake lead to impaired hypothalamic response? Perhaps, this is an attempt to promote efficient energy storage as an 'adaptive' response to the increased availability of food. This mechanism may have developed as a result of evolutionary pressure in keeping with Neel's thrifty genotype hypothesis (Neel, 1999). It is of interest that a similar paradoxical adaptation to overfeeding has also been demonstrated for a peripheral nutrient-sensing pathway whose stimulation appears to decrease mitochondrial function and energy expenditure in response to increased nutrient availability (Obici et al., 2002d).

Recent studies on the metabolic effects of the central administration of insulin (Obici et al., 2002e), leptin (Liu et al., 1998), melanocortins (Obici et al., 2001), and free fatty acids support the notion that these central hypothalamic pathways are also involved in the regulation of hepatic glucose output and insulin action. Since glucose production by the liver is the major source of endogenous fuel, we have postulated that central neural circuitries concomitantly modulate exogenous and endogenous sources of energy in keeping with a negative feedback system designed to monitor and regulate the input of nutrients in the circulation (Obici et al., 2002a). Circulating fatty acids are mostly bound to albumin and cross the blood-brain-barrier (BBB) mainly by simple diffusion in the unbound form. Unbound fatty acids can also be derived via hydrolysis of lipoproteins by lipoprotein lipase within blood or at the cerebral capillary bed. Thus, chylomicrons are likely to be a major circulating source of brain fatty acids in the post-meal state while a combination of unbound fatty acids and locally hydrolyzed lipoproteins contribute to the brain fatty acid pool in the fasting state. A small portion of fatty acid entry into the brain may also occur via direct uptake of lipoprotein particles mediated by lipoprotein receptors in the luminal surface of the cerebro-vascular endothelium (Rapoport, 2001; Qi et al., 2002). Overall, the access of circulating free fatty acids to the central nervous system is generally proportional to their plasma concentration (Miller et al., 1987; Rapoport, 1996) and their concentration in cerebral spinal fluid is ~6% of plasma concentration in fasted anesthetized dog (Goto and Spitzer, 1971). Thus, while one cannot simply extrapolate the effects of ICV oleic acid to physiological conditions, our findings raise the possibility that nutritionally-induced changes in the potent behavioral and metabolic effects of fatty acids within the hypothalamus can contribute to the regulation of both energy balance and insulin action. On the other hand, it has long been recognized that changes in caloric intake have also a dramatic impact on the actions of insulin on glucose metabolism (Pagliassotti et al., 1997). In this regard, hepatic insulin resistance develops within days and/or few weeks following overfeeding in animals and humans (Clore et al., 1995).

Here we report a strong correlation between the inhibition of GP induced by ICV OA and the nutritional status of the animal (i.e. body weight/caloric intake). In the presence of basal insulin levels, stimulation of hypothalamic insulin signaling (Obici et al., 2002e) or central administration of OA (Obici et al., 2002a) leads to inhibition of endogenous glucose production. This 'insulin-like' central effect of LCFAs appears to be at odds with their well-established actions in the peripheral tissues (Boden et al., 1994; Roden et al., 1996; Rebrin et al., 1995). For instance, elevated circulating and hepatic FFA levels reduce insulin suppression of endogenous glucose production (i.e., induces hepatic insulin resistance), whereas elevated levels of central fatty acids enhance the suppression of endogenous glucose production, even in the presence of basal insulin. Similarly, increased availability of fatty acids induces the expression of Glc-6-Pase in the liver (Massillon et al., 1997) while the central administration of OA decreases the hepatic expression of the same enzyme. It is conceivable that central effects of fatty acids provide an important restraint on their peripheral action on hepatic glucose fluxes. Since the central administration of OA failed to inhibit GP in overfed rats, we postulate that the inability of OA to inhibit hepatic glucose production and Glc-6-Pase expression leaves the peripheral effects of fatty acids unopposed by their central effects. It is therefore conceivable that a lack of response to LCFA in the hypothalamus leads to increased rate of glucose output and may contribute to the hepatic insulin resistance observed in this model.

This hypothalamic nutrient sensing may also play a role in fuel partitioning. Under normal conditions, increased availability of fatty acids in the hypothalamus results in decreased output of glucose from the liver (Obici et al., 2002a; 2003) in order to promote the preferential utilization of lipid in muscle and other peripheral tissues. However, when the increased availability of fatty acids is sustained, it triggers the activation of 'thrifty' metabolic mechanisms designed to promote the efficient flux of lipid into energy storage (triglyceride) sites. The increased production of glucose from the liver in overfed rats may serve this goal by providing alternative fuel for oxidation.

The downstream mechanism(s) by which OA modulates hepatic glucose fluxes is yet to be delineated. However, the marked decrease in both in vivo flux through glucose-6-phosphatase and in the hepatic expression of the glucose-6-phosphatase catalytic subunit induced by ICV OA is likely to play a key role. How does lipid sensing within the hypothalamus modulate hepatic glucose fluxes and gene expression? It is likely that rapid changes in autonomic nervous system outflow play a leading role. ICV leptin administration increases autonomic outflow in various regional sites (Liu et al., 1998). It is well known that both sympathetic and parasympathetic systems provide direct innervation of the liver, pancreas, and adipose tissue (via the splanchnic nerve and vagus nerve, respectively). Indeed, ventromedial hypothalamic lesions lead to acute and chronic hyperinsulinemia and this can be reversed by subdiaphragmatic vagotomy (Berthoud and Jeanrenaud, 1979; Inoue and Bray, 1977). Electrical stimulation of the lateral hypothalamus, on the other hand, fails to increase insulin secretion or change plasma glucagon concentration (Berthoud and Jeanrenaud, 1979; Inoue and Bray, 1977; Shimazu et al., 1978). However, it should be pointed out that all present studies were performed in the presence of pancreatic clamp conditions. Thus, it is not likely that changes in the levels of these pancreatic hormones can account for the effects of ICV OA on hepatic glucose fluxes. Of note, electrical stimulation of the ventromedial hypothalamus causes an increase in the activity of PEPCK and Glc-6-Pase, key gluconeogenic enzymes, and a marked suppression of pyruvate kinase, a key glycolitic enzyme in rat liver (Inoue and Bray, 1977; Shimazu, 1996). Stimulation of the lateral hypothalamus, on the other hand leads to a decrease in PEPCK activity. Finally, various adipose depots receive input from autonomic nervous system. The latter has been shown to in turn regulate the gene expression and secretion of fat-derived hormones and cytokines (reviewed in Kahn and Flier, 2000), which have potent effects on insulin action (Combs et al., 2001; Rajala et al., 2003). To this end, the effect of ICV OA on liver glucose-6-phosphatase expression and on hepatic glucose fluxes is reminiscent of those induced by infusion of recombinant adiponectin in mice (Combs et al., 2001). However, we did not detect changes in plasma leptin and plasma adiponectin (Table 2) levels during the ICV injections in any of the experimental groups.

In conclusion, we have shown that the central effects of long-chain fatty acids on food intake and GP are nutritionally regulated. Under normal circumstances biological responses (i.e. changes in food intake and glucose output) keep body fat and glucose homeostasis within a tight range. However, a sustained increase in the availability of nutrients induced a rapid paralysis of (while short-term caloric restriction enhanced) this hypothalamic nutrient sensing system. We postulate that the rapid onset of hypothalamic resistance to multiple nutritional signals such as leptin, insulin, and perhaps fatty acids contributes to the susceptibility to obesity and insulin resistance in predisposed individuals and animals.

Example 4

Role of ATP-Dependent Potassium Channels and the Vagus Nerve in Hypothalamic Regulation of Glucose Production Decreasing Hypothalamic Lipid Oxidation Inhibits Endogenous Glucose Production (GP) via stimulation of K-channels ($K_{ATP}$) and Vagus Nerve. Administration either of the long-chain fatty acid (LCFA) oleic acid (OA) or of inhibitors of CPT-1 activity (CPT1) in the third cerebral ventricle (ICV) inhibits GP. Here, we hypothesize that inhibition of hypothalamic lipid oxidation with CPTi decreases GP via central activation of ATP-dependent potassium channels ($K_{ATP}$) leading to increased vagal input to the liver. To inhibit the entry of LCFA in the mitochondria, we acutely (for 6 h) infused ICV CPTi or its inactive stereoisomer (CON) with (CPTi-GLY and CON-GLY) or without (CPTi and CON) ICV glybenclamide (GLY, $K_{ATP}$ 'blocker') in chronically catheterized S-D rats. All rats also received an IV infusion of [3-$^3$H]-glucose for the last 4 hr of ICV infusion and pancreatic/insulin clamp (insulin 1 mU/kg/min; somatostatin 3 mg/kg/min) during the last 2 hr of each study. In the presence of basal insulin levels, glucose infusion (GIR) was required to prevent hypoglycemia in the CPTi (4.9±1.0 mg/kg/min), but not in the CON (2.1±0.4 mg/kg/min) and CPTi-GLY (1.4±0.5 mg/kg/min) groups. GP was markedly and significantly decreased in CPTi (−47±5% vs. basal; p<0.01; n=7) but not in CON (−15±6%; n=6) or CPTi-GLY (−11±8%; n=6). ICV GLY did not alter GIR and GP in CON-infused rats (not shown). To investigate whether this neural pathway acts via the hepatic branch of the vagus nerve, ICV CPTi or CON infusions were also performed in rats receiving liver-selective vagotomy (LV) or sham-operation (SH). GIR was markedly higher in CPTi-SH (4.7±1.3 mg/kg/min) compared with both CON-SH (1.3±0.4 mg/kg/min) and CPTi-LV (0.8±0.5 mg/kg/min). These differences in GIR were completely accounted for by a marked decrease in GP (−48±2%; P<0.01; n=5) in the CPTi-SH group but not in the CON-SH (−5±3%; n=6) or in the CPTi-LV (−11±4%; n=7) group. LV per se (CON-LV) did not affect GIR and GP. Thus, hypothalamic lipid sensing potently modulates GP via a neural circuitry that requires activation of KAT and vagal input to the liver.

Hepatic "Autoregulation" in Response to Lipid Infusion Requires Central Stimulation of K-channels ($K_{ATP}$) and Liver Vagal Innervation. In the presence of basal insulin levels, increasing plasma long-chain fatty acid levels (LCFA) via lipid infusions stimulates gluconeogenesis (GNG) but does not alter endogenous glucose production (GP) because of a compensatory decrease in hepatic glycogenolysis (GLG) (hepatic "autoregulation"). Since the administration of the LCFA oleic acid in the third cerebral ventricle (ICV) inhibits GP via stimulation of $K_{ATP}$, here we test the hypotheses that: 1) the central activation of $K_{ATP}$ by LCFAs restrains GP during lipid infusions, and 2) that this effect requires hepatic vagal input. To this end, 5 h fasted S-D rats were randomized to receive: IV Intralipid+heparin (IL) (increased LCFA levels by ~3 fold) or saline (S) in combination with ICV Glybenclamide (G) [inhibitor of $K_{ATP}$] or vehicle (C) for 6 h. All rats also received IV infusions of [3-$^3$H]-glucose for the last 4 h and [U-$^{14}$C]-lactate for the last 10 min of the ICV infusion and a pancreatic clamp during the last 2 h of each study. During the clamp period, in the presence of near basal insulin levels (~27 µU/ml), GP (~6 mg/kg.min) was unchanged in S+ICVC, S+ICVG or IL+ICVC. Lipid infusion with either ICVC or ICVG increased GNG but only IL+ICVG failed to inhibit GLG, leading to increased GP (to 9.8±0.3; P<0.001). To examine whether the central effects of LCFA on GP are mediated by vagal stimulation, we next repeated the lipid infusion studies in rats with selective hepatic vagotomy (HV). During the pancreatic clamp period, GP (~6 mg/kg/min) was similar in S-treated HV and S or IL treated sham-operated rats. Importantly, IL increased GP to 9.7±0.5 (P<0.001) in HV, recapitulating the effect ICVG. Glucose utilization was similar in all groups.

In summary, hypothalamic $K_{ATP}$ and hepatic vagus nerve are required for peripheral LCFA-induced hepatic glucose "autoregulation". Thus, we postulate that systemic hyperlipidemia activates a central lipid-sensing pathway that potently modulates GP via a neural circuitry that requires activation of central $K_{ATP}$ and descending vagal efferent input to the liver.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference in their entireties. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NO: s

SEQ ID NO:1 - Ribozyme

ACAGCACGCCGCUCUGAUGAGUCCGGUGAGGACGAAACCACGUUCUUCGUC

SEQ ID NO: 2 - Ribozyme

CTGTACCAAAGAGCTGATGAGTCCGTGAGGACGAAACGCCGCTCACAATGA

SEQ ID NO: 3 - Ribozyme

CATTGTGAGCGGCGTTTCGTCCTCACGGACTCATCAGCTCTTTGGTACAGA

SEQ ID NO: 4 - Random sequence

GGAGCCTCGAGATCTGATGAGTCCGTGAGGACGAAACTGTGAGCGTTTGG

SEQ ID NO: 5 - CPT1L forward primer

CTCCGAGCTCAGTGAGGACCTAAAG-3'

SEQ ID NO: 6 - CPT1L reverse primer

CAAATACCACTGCAATTTGTG

SEQ ID NO: 7 - CPT1M forward primer

CCAGACTGCAGAAATACCTGGTGCTC

APPENDIX-continued

SEQ ID NO: s

SEQ ID NO: 8 - CPT1M reverse primer

GTTCTGACGTGCTTCTGCCCACTCTAC

SEQ ID NO: 9 - NPY forward primer

GCCATGATGCTAGGTAACAAACG

SEQ ID NO: 10 - NPY reverse primer

GTTTCATTTCCCATCACCACATG

SEQ ID NO: 11 - POMC forward primer

CCAGGCAACGGAGATGAAC

SEQ ID NO: 12 - POMC reverse primer

TCACTGGCCCTTCTTGTGC

SEQ ID NO: 13 - AgRP forward primer

GCCATGCTGACTGCAATGTT

SEQ ID NO: 14 - AgRP reverse primer

TGGCTAGGTGCGACTACAGA

SEQ ID NO: 15 - β-actin forward primer

TGAGACCTTCAACACCCCAGCC

SEQ ID NO: 16 - β-actin reverse primer

GAGTACTTGCGCTCAGGAGGAG

---

What is claimed is:

1. A method of reducing food intake in a mammal, the method comprising administering to the mammal a pharmaceutical composition comprising a small molecule capable of inhibiting carnitine palmitoyl transferase 1 (CPT1) in the brain of a mammal, wherein the pharmaceutical composition is administered in an amount and manner effective to reduce food intake in the mammal, wherein the pharmaceutical composition is administered to the brain such that the small molecule enters the hypothalamus or the pharmaceutical composition is administered such that the small molecule crosses the blood brain barrier, and wherein the small molecule capable of inhibiting CPT1 is 2-tetradecylglydate (TDGA) or (R)-N-(tetradecylcarbamoyl)-aminocarnitine.

2. The method of claim 1, wherein the small molecule capable of inhibiting CPT1 is 2-tetradecylglydate (TDGA).

3. The method of claim 1, wherein the small molecule capable of inhibiting CPT1 is (R)-N-(tetradecylcarbamoyl)-aminocarnitine.

* * * * *